United States Patent [19]

Fife et al.

[11] Patent Number: 5,652,336
[45] Date of Patent: Jul. 29, 1997

[54] POLYMER-BOUND MIXED CARBOXYLIC ANHYDRIDES AS A STABLE FORM OF ACTIVATED CARBOXYLIC ACIDS

[75] Inventors: Wilmer K. Fife; Daniel F. Shullenberger, both of Indianapolis,, Ind.

[73] Assignee: Indiana University Foundation, Bloomington, Ind.

[21] Appl. No.: 620,936

[22] Filed: Mar. 22, 1996

Related U.S. Application Data

[62] Division of Ser. No. 235,192, Apr. 29, 1994, Pat. No. 5,516,892, which is a continuation of Ser. No. 997,454, Dec. 28, 1992, abandoned.

[51] Int. Cl.$^6$ .............................. C07K 1/08; C07C 51/56
[52] U.S. Cl. ..................... 530/342; 530/333; 530/334; 562/887; 562/888; 562/894
[58] Field of Search .................................... 530/342, 333, 530/334; 562/887, 888, 894

Primary Examiner—Cecilia J. Tsang
Assistant Examiner—David Lukton
Attorney, Agent, or Firm—Clifford W. Browning; Woodard, Emhardt, Naughton Moriarty & NcNett

[57] ABSTRACT

Polymer-bound mixed carboxylic anhydrides can be prepared under mild conditions by the condensation of carboxylic acids (including N-protected amino acids) with polymer-bound acid chlorides. These mixed anhydrides function as polymeric reagents in the sense that they will react readily with monomeric nucleophiles such as amines to form amide or peptide products, depending on the identities of the mixed anhydride and amine reactants. However, in spite of their reactivity, these polymeric mixed anhydrides exhibit a significant degree of stability under conditions of prolonged storage, which suggests that such compounds have commercial utility as a relatively stable form of highly activated carboxylic acids. The polymeric support can be reactivated and recycled for repeated use in the derivatization process.

15 Claims, 17 Drawing Sheets

A.

Resin–CH$_2$O–COCl

↓ 1.2 eq. RCO$_2$H, 1.2 eq. NR$_3$

Resin–CH$_2$O–CO$_2$COR

↓ 1.0 eq. RCO$_2$H, 1.0 eq. NR$_3$

Resin–CH$_2$OH + CO$_2$ + (RCO)$_2$O

75–90%

(Shambu, Digenis, JCS Chem. Comm. 1974, 619)

B.

↓ 1.0 eq. –CO$_2$H, 1.0 eq. NR$_3$

80%

(Martin et al, J.Org. Chem. 43, 4571 [1978])

5,652,336

POLYMER-BOUND MIXED CARBOXYLIC ANHYDRIDES AS A STABLE FORM OF ACTIVATED CARBOXYLIC ACIDS

This application is a division of application Ser. No. 08/235,192, filed Apr. 29, 1994, now U.S. Pat. No. 5,516,892 which is a continuation of application Ser. No. 07/997,454 filed Dec. 28, 1992, now abandoned.

BACKGROUND OF THE INVENTION

Synthetic copolymers, such as those based on styrene and acrylate derivatives, have found widespread use as solid supports in e number of techniques of fundamental importance in modern biochemistry and related biomedical fields. Examples of such well-studied and refined methodologies include affinity chromatography, immobilized enzyme technology, and the solid-phase synthesis of nucleic acids and peptides. Most pertinent to the background of the present invention is the last of these examples, commonly known as solid-phase peptide synthesis (SPPS). The method of SPPS involves the stepwise construction from the C-terminus of a polymer-bound protected peptide, followed by its deprotection and release from the polymeric support to yield the free peptide, as illustrated in FIG. 1. The advantages of this approach are well documented and include the facile removal of reagents and by-products from the peptide intermediates at each stage of the synthesis, and the amenability of the method to automation.

First described by Merrifield in 1963, R. B. Merrifield, *J. Am. Chem. Soc.* 85, 2149 (1963), the method of SPPS represented a major advance in the field of peptide chemistry. Although many of the techniques and protocols associated with the method of SPPS have since been refined to such a degree that a vast number of peptides can be prepared on polymeric resins in routine fashion using sophisticated automated synthesizers, the Merrifield method does not lend itself well to some applications, such as the bulk synthesis of peptides on an industrial scale, and the condensation of peptide fragments. There is, therefore, an ongoing need for methods to complement Merrifield's SPPS approach.

One area of research that showed promise in this regard involved the use of polymeric reagents in peptide bond formation. This approach represented a fundamental departure from the Merrifield strategy in the sense that an insoluble polymeric support was utilized not simply as an anchor for the growing peptide but, in fact, participated in the coupling step as the activated carboxyl component. In this method, the protected peptide product is released into solution after coupling and can be separated from the polymeric resin by simple filtration. The first example of this approach was described by Fridkin et al. in 1966, M. Fridkin, A. Patchornik, E. Katchalski, *J. Am. Chem. Soc.* 88, 3164 (1966). Fridkin et al. examined the preparation of polymer-bound o-nitrophenyl active esters of N-blocked amino acids and the use of these reagents in the synthesis of a series of small protected peptides, as illustrated in FIG. 2. Since then, the application of such reagents to peptide synthesis has been investigated in a number of laboratories using a variety of polymeric active esters, as well as polymeric coupling agents. This method has, in some respects, emerged as a useful alternative to the Merrifield method. Among the advantages of the polymeric reagent approach cited by Patchornik et al., A. Patchornik, E. Nov, K. A. Jacobson, Y. Shai, "Polymeric Reagents and Catalysts," W. T. Ford, ed., ACS Symposium Series No. 308, are rapid, high-yield coupling reagents, peptide products of exceptional purity, and the option of recycling the used polymeric resin.

Within the realm of polymeric reagents applied to peptide synthesis, one area that has been virtually ignored, however, is the use of polymeric mixed anhydrides despite the fact that in solution-phase peptide chemistry amino acid activation through mixed anhydride formation represents a well-established method of peptide bond formation. J. Meienhofer, *The Peptides*, 1, 263–314 (Acedemic Press 1979).

The scientific literature contains several reports describing various types of polymer-bound mixed anhydrides that demonstrate the potential synthetic utility of such reagents. The synthesis and application of resin supported mixed anhydrides were described by G. E. Martin, et al., *J. Org. Chem.* 43, 4571 (1978), and S. Boivin, et al., *Bull. Soc. Chim. France* II, 201 (1984), but the materials of these reports lack the chemical stability required to make them viable general reagents. The synthesis and application of resin supported mixed carboxylic acids were described by M. B. Shambhu, et al., *Tetrahedron Lett.* 31, 143, (1973), and M. B. Shambhu, et al., *J. Chem. Soc. Chem. Commun.* 619, (1974), but the materials of these reports produce slow and incomplete reactions. The mixed anhydrides of these published reports are also unselective toward derivatizing reagents. Hence, high levels of unproductive reaction occur at the resin, which makes the resin difficult, if not impossible to recycle.

Activation of N-blocked α-amino acids via mixed anhydrides has also been known since 1950. See, T. Wieland et al., *Ann*, 569, 117 (1950). Unfortunately, the instability, both structural and chemical, of these intermediates forced workers to develop more useful alternatives, which typically have included: (1) coupling methods that activate the carboxyl group in situ, or (2) the formation of alternative activated intermediates such as acid chlorides, acid fluorides, active esters or mixed anhydrides of chloroformates.

The only known published example of the application of polymeric mixed anhydrides to peptide synthesis is the published work of V. K. Haridasan et al., *J. Org. Chum.* 52, 2662 (1987), who described the preparation of (o-$NO_2$)Cbz-L-Phe-Gly-OEt using a polymeric dithiocarbonic-carboxylic acid mixed anhydride. The reagents of this method are mixed anhydrides of a carboxylic acid and a resin-supported dithiocarbamic acid. The Haridasan et al. method also requires the prior activation of the carboxylic acid to an acid chloride followed by formation of the mixed anhydride by reaction with the resin-supported dithiocarbamate salt. However, many carboxylic acids, including N-blocked amino acids, form unstable acid chlorides. Consequently, the common belief has been that resin-supported acid chlorides are not particularly useful as reagents. No known published examples of mixed anhydrides of N-blocked amino acids and resin-supported carboxylic acids have been reported, for example. The assumption has been that such materials would be unstable even if a synthetic route to them was discovered.

SUMMARY OF THE INVENTION

The reagents of the present invention are mixed anhydrides of two carboxylic acids, one of which may be an N-blocked amino acid, and the other a resin-supported carboxylic acid. In contrast to the prior art, the reagents of the present invention are produced directly from the carboxylic acids, including N-blocked amino acids, and a resin-supported acid chloride. Carboxylic acids are activated and converted to stable resin-supported mixed anhydrides in just one step to produce reagents having all the usual benefits of stable, recyclable, resin-supported reagents. Formation of the mixed anhydride reagents of the present invention requires no prior activation of the carboxylic acids, including N-blocked amino acids, which is a particular and significant benefit of the present invention.

The polymer-bound mixed anhydrides of the present invention have been prepared from Merrifield's resin (crosslinked poly(chloromethylstyrene)), functionalized with acid chloride groups, and carboxylic acids. Particular interest has been directed to the polymer-supported mixed anhydrides of N-blocked α-amino acids. These activated intermediates have exhibited significant levels of chemical stability during storage and are useful for synthesis of amide, ester and peptide derivatives of the amino acid. The present invention represents a new and particularly effective means of activating N-blocked α-amino acids in structurally and chemically stable forms that can be handled like conventional laboratory agents and utilized for conversion to important derivatives. The chirality of the amino acid appears to be unaffected by the process, and the polymeric support can be reactivated and recycled for repeated use in the derivatization process.

According to a preferred embodiment of the present invention, polymer-bound mixed carboxylic anhydrides can be prepared under mild conditions by the condensation of carboxylic acids (including N-protected amino acids) with polymer-bound acid chlorides. These mixed anhydrides function as polymeric reagents in the sense that they will react readily with monomeric nucleophiles such as amines to form amide or peptide products, depending on the identities of the mixed anhydride and amine reactants. However, in spite of their reactivity, these polymeric mixed anhydrides exhibit a significant degree of stability under conditions of prolonged storage, which suggests that such compounds have commercial utility as a relatively stable form of highly activated carboxylic acids. The polymeric support can be reactivated and recycled for repeated use in the derivatization process.

One embodiment of the present invention is a method for producing a stable, polymer-bound mixed carboxylic-carboxylic acid anhydride of N-blocked amino acids, comprising the reaction of a polymer-bound acid halide derived from a recyclable polymer-bound carboxylic acid with an N-blocked amino acid salt, whereby the N-blocked amino acid is activated and converted to a polymer-bound mixed carboxylic-carboxylic acid anhydride of the N-blocked amino acid.

Another embodiment of the present invention is a method for the synthesis of protected peptide derivatives of N-blocked amino acids, comprising, providing a polymer-bound mixed carboxylic-carboxylic acid anhydride of an N-blocked amino acid of the formula

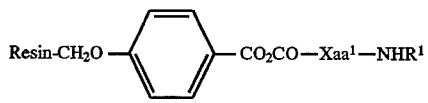

by the reaction of a polymer-bound acid halide of the formula

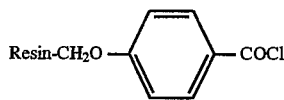

derived from a polymer-bound carboxylic acid with an N-blocked amino acid salt of the formula

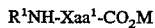

whereby the N-blocked amino acid is activated and converted to a polymer-bound mixed carboxylic-carboxylic acid anhydride of the N-blocked amino acid;

directly reacting said polymer-bound mixed carboxylic-carboxylic acid anhydride with an amine component of the formula

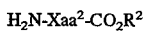

separating the liquid phase of the reaction mixture from the polymer by filtration;

and extracting from the liquid phase a protected peptide of the formula

In the foregoing formulas, $R^1$ represents an amino blocking or protecting group;

$R^2$ represents a carboxyl blocking or protecting group;

-NH-Xaa$^1$-CO- represents an amino acid residue;

-NH-Xaa$^2$-CO- represents an amino acid residue; and $R^1$-NH-Xaa$^1$-CO$_2$M represents a salt of an N-blocked or N-protected amino acid.

More broadly, and in accordance with the present invention, the synthesis of protected peptide derivatives of N-blocked amino acids can be carried out using a polymer-bound acid halide of the following formula, and applying the process as indicated above:

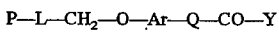

wherein P represents a polymeric solid support;

L represents a covalent bond or a linker moiety;

Ar represents a phenylene moiety, optionally substituted with an alkoxy group;

Q represents a covalent bond or —CH=CH—; and

Y represents a halogen.

The present invention should be particularly useful in coupling peptides of 15 or more amino acids available from commercial synthesizers to make longer peptides of high purity. The reaction of polymer-supported N-blocked activated peptide with C-blocked peptide should give products of high purity since side products should be cleanly and easily separated from these peptides.

It is an object of the present invention to provide polymer-bound mixed carboxylic anhydrides that can be stored at room temperature for extended periods of time prior to use, and that are stable when exposed to water-organic solvent mixtures.

It is a further object of the present invention to provide polymer-bound mixed carboxylic anhydrides in which the spent polymeric resin can be easily recycled by direct conversion back to the polymeric acid chloride after being used in a coupling reaction.

It is a further object of the present invention to provide polymer-bound mixed carboxylic anhydrides that use a polymer-supported acid halide (e.g., fluoride, chloride) derived from a carboxylic acid of relatively low electrophilicity, e.g., cinnamic acid, p-alkoxybenzoic acid, which provides mixed anhydrides with N-blocked α-amino acids that highly favor attack at the carbonyl of the latter acids by amines and α-amino acid esters.

It is a further object of the present invention to provide polymer-bound mixed carboxylic anhydrides that use polymer-supported cinnamic and p-alkoxybenzoic acids that provide a "spacer linkage" that separates the reactive carboxyl and acid halide groups from the polymeric framework of the resin and permits rapid, efficient access of solution reagents to them.

It is a further object of the present invention to provide polymer-bound mixed carboxylic anhydrides that demonstrate lack of racemization of chiral reactants during the coupling procedure, which permits use of the methodology of the invention in coupling enantiomerically pure reactants such as individual N-blocked amino acids as well as longer peptides of different amino acid content.

It is a further object of the present invention to provide polymer-bound mixed carboxylic anhydrides in which the stability of the resin-bound activated amino acids and the ability to cleanly separate resin-bound materials from unreacted starting materials and other contaminants in solution permits synthesis and isolation of synthetic peptides of exceptional purity.

It is a further object of the present invention to provide a method for producing a stable, polymer-bound mixed carboxylic-carboxylic acid anhydride, comprising the reaction of a recyclable, polymer-bound carboxylic acid and a carboxylic acid salt that contains no additional nucleophilic groups such as amino or hydroxyl groups.

Related objects and advantages of the present invention will be evident from the following description.

DESCRIPTION OF THE PREFERRED EMBODIMENTS

Figure 1:
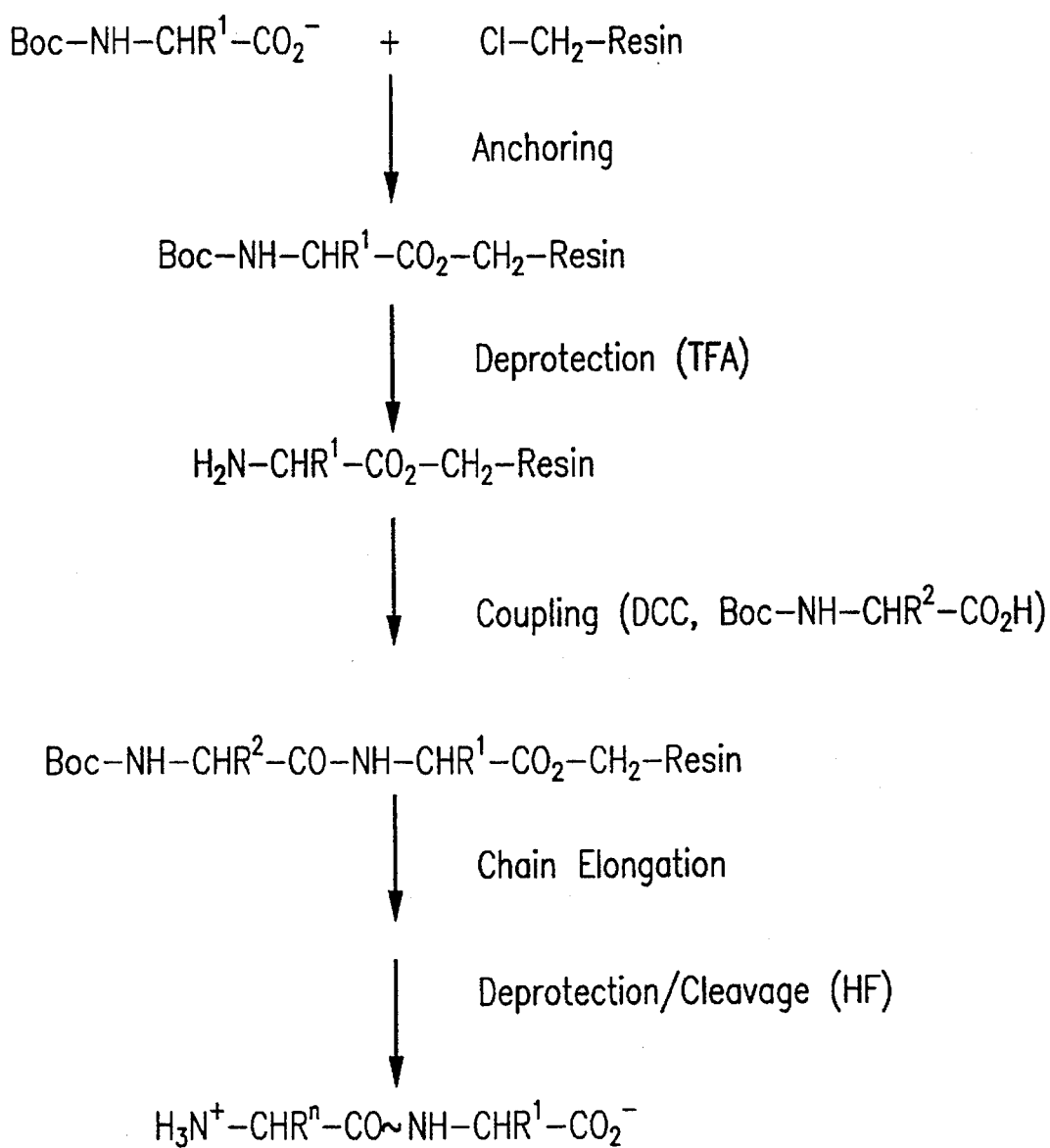
FIG. 1 is an illustration of the Merrifield method of solid-phase peptide synthesis (SPPS) and is a prior art illustration.
Figure 2:
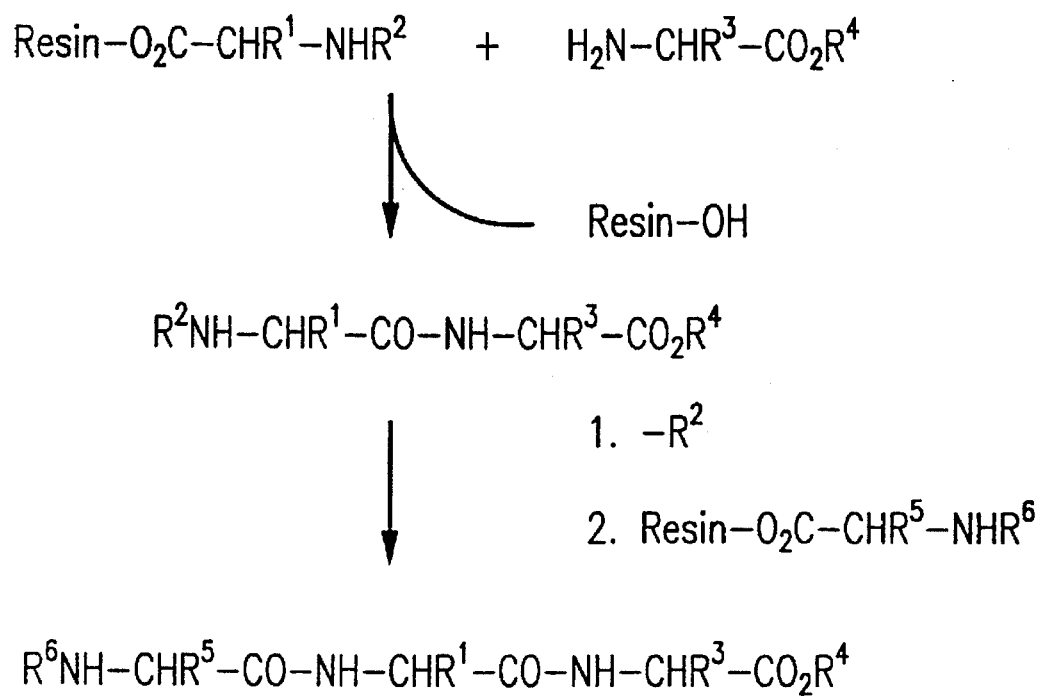
FIG. 2 is an illustration of polymeric active esters in peptide synthesis, and is a prior art illustration.

For the purposes of promoting an understanding of the principles of the invention, reference will now be made to the preferred embodiments of the invention and specific language will be used to describe the same. It will nevertheless be understood that no limitation of the scope of the invention is thereby intended, such alterations and further modifications of the preferred embodiments, and such further applications of the principles of the invention being contemplated as would normally occur to one skilled in the art to which the invention relates.

Experimental work completed to date has demonstrated that monomeric mixed carboxylic-carboxylic acid anhydrides of N-blocked amino acids (2) function quite ably as activated carboxyl components in the preparation of protected peptides under phase-transfer conditions. A key principle that emerged from this work is that these mixed anhydrides show a high degree of regioselectivity, manifested by the preferential reaction of nucleophilic amine components at the amino acid carbonyl to yield the desired peptide products. This is a paramount consideration for any mixed anhydride procedure, and in this case, the observed regioselectivity appears to be derived from the aromatic nature of the p-toluic, o-toluic, or cinnamic acid that participates with the amino acid derivative in the mixed anhydride. On the basis of these findings, further experimental work was conducted in which polymer-bound mixed anhydrides analogous to 2 were prepared to combine the observed chemical characteristics of the monomeric species with the previously noted practical advantages of a polymeric reagent.

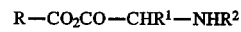

Initial efforts involved the synthesis of a polymer-bound cinnamic acid 3 from commercially available Merrifield chloromethylated polystyrene resin. The choice of a cinnamic acid structure was based not only on its previously demonstrated utility in a monomeric anhydride, but also on the premise that the rigid vinyl benzene skeleton would serve as an effective "spacer arm" to extend the chemically reactive sites of the polymeric reagent out from the polymeric backbone. The so-called pendant carboxyl group of 3 was converted to the corresponding acid chloride functionality (4) after which preparation of a mixed anhydride was achieved by condensation of 4 with a pyridine salt of benzoic acid to yield 5a. Preparation of the polymeric mixed anhydride of Boc-L-Ala (5b) was carried out in an analogous manner.

It was subsequently determined that, as expected, both 5b and the corresponding Boc-L-Val mixed anhydride 5c could react with C-protected amino acids to yield the desired dipeptide derivatives as determined by thin-layer chromatography (TLC). Interestingly, attempts to prepare the N-benzoyl-protected alanine anhydride 5d using the same method were less successful, a development that will be treated in more detail below,

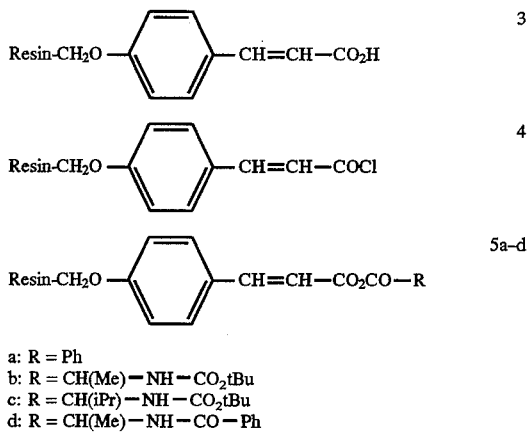

a: R = Ph
b: R = CH(Me)—NH—CO$_2$tBu
c: R = CH(iPr)—NH—CO$_2$tBu
d: R = CH(Me)—NH—CO—Ph

Attempts to optimize the cinnamic acid system exposed difficulties at the acid chloride and mixed anhydride stages that could not be entirely remedied and led to the development of an analogous system based on a polymer-bound benzoic acid functionality (6), which appeared to be an improvement over its cinnamic acid predecessor. The benzoic acid resin was subsequently employed in a series of experiments that addressed the effect of such variables as amino acid side chain, N-protecting group of the amino acid, and degree of resin functionalization on the overall synthetic yield of the polymeric mixed anhydride. The results of these experiments defined a two-stage activation/coupling protocol for peptide bond formation employing the polymer-bound benzoyl chloride 7.

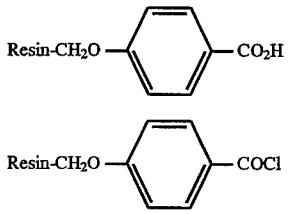

It will be evident from the following discussion that most of the experimental data supporting the present invention is provided by the techniques of Fourier-Transform infrared spectroscopy (FT-IR) and elemental analysis. These techniques readily lend themselves to the analysis of polymeric materials, and they have proved indispensable to the work described herein as a means of monitoring changes in the polymeric resin. The FT-IR analysis of polymeric species related to polymeric resins 3 and 6 with particular emphasis on carbonyl absorption bands has permitted a qualitative evaluation of changes in the pendant functional groups for any given treatment of the polymeric resin while in complementary fashion data derived from determination of the N and/or Cl content of the resin was utilized to assess the efficiency of the same processes in a quantitative sense.

The Polymer-Bound Cinnamic Acid System

Figure 3:
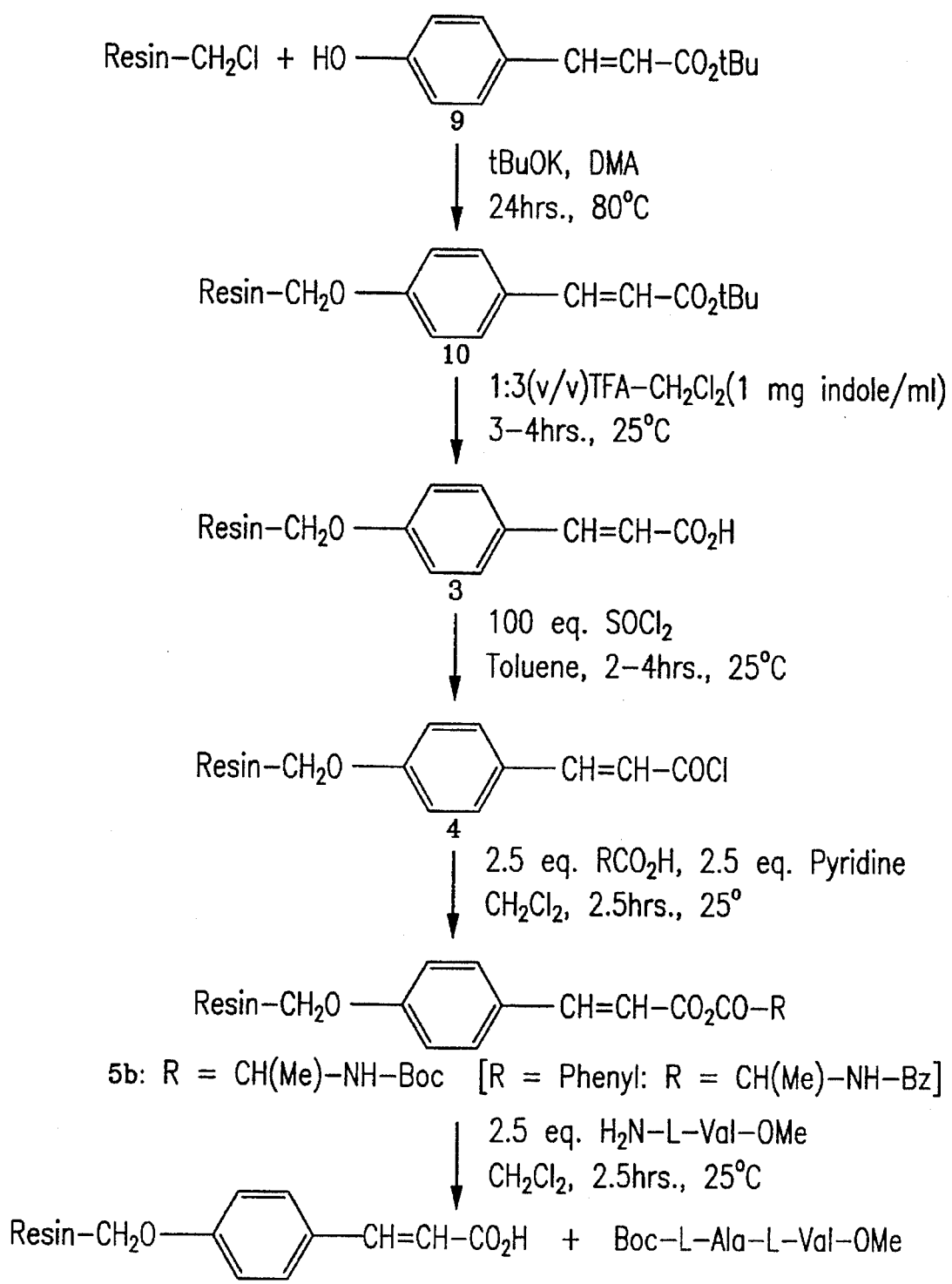
FIG. 3 is an illustration of peptide synthesis via the polymer-bound cinnamic acid system of the present invention.

The initial construction of cinnamic acid-based polymeric mixed anhydrides, culminating in the preparation of the protected dipeptide Boc-L-Ala-L-Val-OMe, is summarized in FIG. 3. At each step of the process the resin intermediate was analyzed first by FT-IR spectroscopy and subsequently characterized on a more quantitative basis, using in most cases elemental microanalysis.

Figure 4:
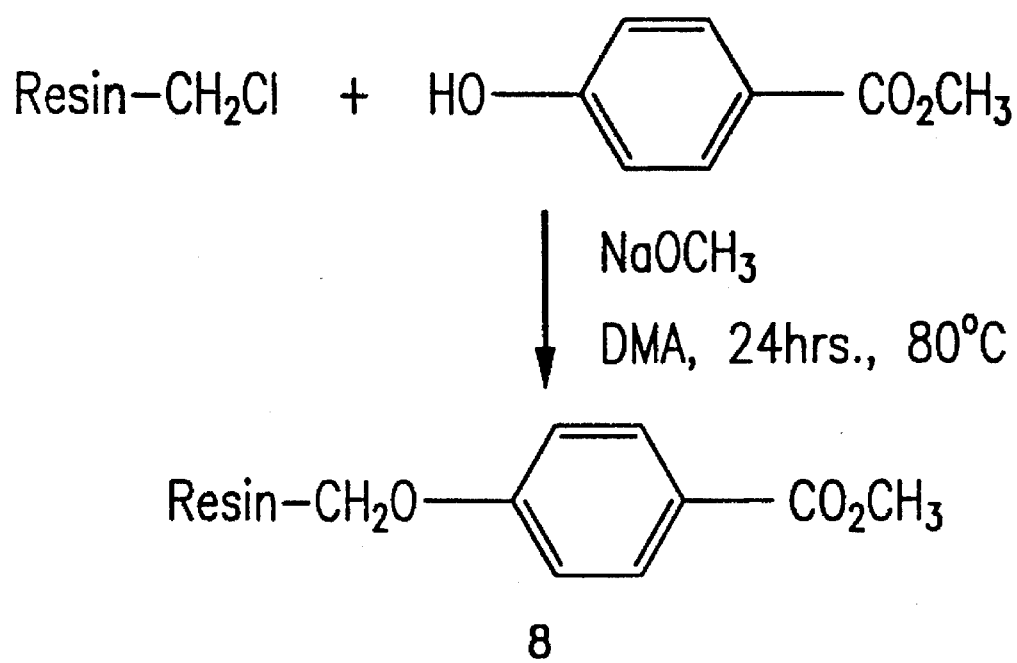
FIG. 4 is an illustration of the preparation of methyl p-alkoxybenzoate resin via the method of Wang.

The first consideration in the preparation of a polymeric reagent containing a covalently bound cinnamic acid functionality was to determine a method for attachment of the cinnamic acid nucleus through its aromatic ring to a polymeric backbone and to leave the carboxyl group free to participate in mixed anhydride chemistry of the type previously discussed. One approach which suggested itself for this application was the method previously employed by Wang, S. S. Wang, J. Am. Chem. Soc. 95, 1328–1333 (1973), for the preparation of a methyl p-alkoxybenzoate resin (8), summarized in more detail in FIG. 4, an intermediate in the synthesis of the corresponding p-alkoxybenzyl alcohol resin. In the Wang procedure, the methyl p-alkoxybenzoate entity is covalently introduced to the polymer by a straightforward O-alkylation process involving nucleophilic attack by the sodium salt of methyl 4-hydroxybenzoate on the chloromethyl functionality of commercial Merrifield resin to yield an aryl alkyl ether linkage.

Adaptation of the Wang approach to the introduction of a cinnamic acid group into the polymer required a phenolic analog of cinnamic acid, taking into account the need to protect the carboxyl group in a form that would permit its facile regeneration in a subsequent step. Protection of the carboxyl as a tert-butyl ester in conjunction with deprotection by trifluoroacetic acid (TFA) presented itself as a means of meeting that condition, given both the previously demonstrated lability of tert butyl esters to TFA, and the well-established utility of TFA in solid-phase synthetic schemes.

Commercially obtained trans p-hydroxycinnamic acid was converted to the corresponding tert-butyl ester (9) (FIG. 3) by treatment with isobutylene and p-toluenesulfonic acid as described by Bodanszky, M. Bodanszky, The Practice of Peptide Synthesis (Springer-Verlag, New York 1984). Referring to FIG. 3, in a slightly modified version of the Wang procedure, the ester 9 was subsequently treated with potassium tert-butoxide (tBuOK) in dimethylacetamide (DMA) to generate the potassium phenolate salt of 9, which was in turn reacted in a molar ratio of 2.5:1.0 with the Merrifield chloromethyl resin at 80° C. for 24 hours. After the reaction, the resin was filtered, washed, and dried in vacuo for 5 hours then analyzed in the form of a KBr pellet by FT-IR spectroscopy. The spectrum of the resin product showed the appearance of a strong carbonyl band at 1706.5 cm$^{-1}$ indicating the introduction of the tert-butyl ester functionality thereby providing a qualitative confirmation of the product's identity as the desired tert-butyl p-alkoxycinnamate resin 10.

Continuing to refer to FIG. 3, cleavage of the ester group of the newly formed tert-butyl p-alkoxycinnamate resin was attempted using a 1:3 TFA-CH$_2$Cl$_2$ (v/v; 1 mg indole/ml) solution, which has been used extensively in SPPS for the removal of tert-butyloxycarbonyl (tBoc) N-protecting groups. Treatment of resin 10 with this TFA reagent for 30 minutes at room temperature in accordance with standard SPPS protocols for the removal of Boc groups yielded a resin product that was examined by FT-IR. Although clear differences were evident in the spectra of the resin before and after the TFA treatment, the presence of still-intact tert-butyl ester functionalities was indicated by a carbonyl band of significant intensity in the latter at roughly 1706 cm$^{-1}$. On this basis, a second 30 minute TFA treatment of the resin was carried out, yielding a product, which as before, was analyzed by FT-IR. The resultant spectrum displayed additional changes in the form of a new jagged band of moderate intensity in the carbonyl region. From this absorption pattern two distinct peaks appearing at 1685 cm$^{-1}$ and 1717 m could be identified, a circumstance quite analogous to that observed in the analysis of other polymer-bound carboxyl functionalities where similar bands at 1685 cm$^{-1}$ and 1715 cm$^{-1}$ have been correlated with the hydrogen-bonded and monomeric forms respectively of a pendant carboxylic acid. Treatment of the resin a third time with TFA for 30 minutes in the same fashion as before did not result in any discernable changes in terms of FT-IR analysis, indicating that the removal of the tert-butyl ester to yield the unprotected polymer-bound cinnamic acid 3 had been effectively complete after the second TFA deprotection treatment. In subsequent attempts to prepare 3 it was found that the conversion of larger quantities of 10 to 3 required reaction times longer than the 60 minutes (total) exposure utilized in this case, so the TFA deprotection step was eventually extended to 3–4 hours without any noticeable deleterious effects.

Continuing to refer to FIG. 3, the activation of resin 3 by conversion to the corresponding polymer-bound cinnamoyl chloride 4 utilized $SOCl_2$. Accordingly, a weighed sample of resin 3 was treated with a large excess (49 eq) of $SOCl_2$ in toluene at room temperature for 60 minutes after which the liquid phase was removed and the resin treated an additional two times in the same manner with fresh $SOCl_2$-toluene. Afterward, the resin was washed, dried in vacuo, and analyzed by FT-IR. The resultant spectrum of this material revealed a new carbonyl band of moderate intensity marked by small yet distinct peaks at 1735.0, 1739.4, and 1752.0 cm$^{-1}$. The shape of the carbonyl band in the resin product bore a clear resemblance to that of the monomeric cinnamoyl chloride, providing support for the assignment of structure 4 to the former. Subsequent efforts to convert 3 by the above $SOCl_2$ treatment yielded resin products of identical spectral character, thereby confirming the reproducibility of the method.

Phase-transfer methods for the synthesis of monomeric mixed anhydrides from aromatic acid chlorides utilized sodium salts of N-protected amino acids, but the analogous use of trialkylammonium salts of the latter has been well established as an efficient means of generating mixed anhydrides in nonaqueous systems which, given the swelling properties of polystyrene resins, is an important consideration in this case. Conversion of 4 to a polymeric mixed anhydride was accomplished by treatment of the former in methylene chloride with. 2.5 eq of a model carboxylate salt generated from benzoic acid, and pyridine. It may be noted parenthetically that the use of pyridine in this case was prompted by its weak basicity, which is an important element in preventing racemization among highly activated N-protected amino acids. After 4 was exposed to the pyridinium benzoate for 1.5 hours at room temperature the resin was filtered, washed, and dried in the usual manner, then examined by FT-IR. The spectrum obtained showed two sharp carbonyl bands at 1719.0 cm$^{-1}$ and 1782.6 cm$^{-1}$ which was quite consistent with previous data for aromatic mixed anhydrides of both the monomeric and polymeric reagent types. On the basis of the FT-IR analysis the resin derived from 4 was assigned structure 5a, the expected polymeric mixed anhydride product. The method was subsequently applied without modification to the synthesis of resin-bound mixed anhydrides of N-protected amino acids. Preparation of the mixed anhydride 5b was readily achieved by treatment of 4 with the pyridinium salt of Boc-L-Ala in the same manner as employed in the synthesis of 5a. Identification of the product thus obtained was based on FT-IR analysis, which showed the appearance of three new carbonyl bands at 1718.3 cm$^{-1}$, 1783.9 cm$^{-1}$ and 1803.1 cm$^{-1}$, a situation consistent with the joint incorporation of anhydride and urethane functionalities at pendant sites of the polymer. It was similarly shown that the analogous mixed anhydride of Boc-L-Val (5c) could be prepared in like fashion yielding upon examination by FT-IR a comparable spectrum marked by carbonyl bands at 1722.3 cm$^{-1}$, 1783.0 cm$^{-1}$ and 1799.5 cm$^{-1}$.

An interesting adjunct to these results was observed when benzoyl-L-alamine (Bz-L-Ala) was reacted with 4 to prepare the polymeric mixed anhydride 5d. Despite using the same procedure that produced anhydride resins 5a–5c with their characteristically clean FT-IR spectra, the resin product in this case gave rise to a considerably less conclusive spectrum in which the presumed anhydride bands (1702.1 cm$^{-1}$ and 1779.6 cm$^{-1}$) were accompanied by additional carbonyl bands at 1685.3 cm$^{-1}$ and 1717.7 cm$^{-1}$, suggesting the presence of a significant amount of free carboxyl functionalities. Further attempts to prepare 5d in this manner gave similar results indicating that N-benzoyl amino acids are less useful in the preparation of polymeric mixed anhydrides than the corresponding N-Boc amino acids. One possible explanation for this is the greater tendency of N-benzoyl amino acids to undergo cyclization to azlactones since, in polymeric reagents of this sort, azlactone formation would result in loss of amino acid from the resin upon carboxyl activation. Additional experiments with resin 4 and its benzoyl chloride analogue 7 supported this view.

With respect to the polymeric mixed anhydrides of Boc-L-Ala and Boc-L-Val further support for the structural assignments of 5b and 5c was obtained from the preparation and analysis of the model monomeric anhydride 11 derived from the condensation of Boc-L-Val and cinnamoyl chloride. The FT-IR spectrum of 11 revealed a carbonyl pattern very similar to that of 5c, in accordance with expectations.

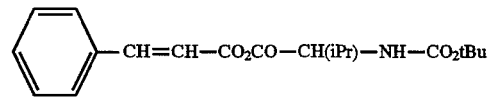

11

Having established that it was possible to reproducibly prepare and isolate mixed anhydrides of N-protected amino acids from 4, attempts to utilize these polymeric reagents for peptide synthesis were undertaken. Accordingly, referring again to FIG. 3, a sample of 5b was swollen in methylene chloride, then treated with 2.5 eq of $H_2$N-L-Val-OCH$_3$ in the same solvent at room temperature. After a reaction time of 1.5 hours, the liquid phase was removed from the resin by filtration and immediately analyzed by thin-layer chromatography (TLC). The resultant chromatogram of this filtrate revealed two spots, one of $R_f$ corresponding to (excess) $H_2$-N-L-Val-OCH$_3$, and a second of $R_f$ 0.88, which was identical to that of an authentic sample of Boc-L-Ala-L-Val-OMe. The methylene chloride solution containing the product was subsequently extracted with dilute aqueous acid and base, dried over $MgSO_4$ and examined a second time by TLC. Confirming the removal of the contaminating $H_2$N-L-Val-OCH$_3$, a single spot ($R_f$ 0.88) was observed, which as before comigrated with authentic Boc-L-Ala-L-Val-OCH$_3$. On this basis, it was concluded that the desired protected dipeptide Boc-L-Ala-L-Val-OCH$_3$ had been successfully prepared using the polymeric mixed anhydride 5b. A subsequent experiment confirmed this result by demonstrating not unexpectedly that the same dipeptide could be prepared by a modified procedure in which the intermediate mixed anhydride 5b was not isolated as before but instead reacted directly with the amine component H$_2$N-L-Val-OCH$_3$. In this case as previously the presence of Boc-L-Ala-L-Val-OCH$_3$ was confirmed by TLC data.

Evidence of improved yield was obtained from crops of 4 prepared via an alternate method using (COCl)$_2$. Efforts to utilize (COCl)$_2$ were initially quite similar to those employed previously in the preparation of 4 with SOCl$_2$. Treatment of a weighed sample of the polymer-bound cinnamic acid 3 with an excess (20 eq) of (COCl)$_2$ in toluene was carried out at room temperature for 60 minutes after which the liquid phase was filtered off and the resin treated with fresh (COCl)$_2$-toluene for an additional 60 minutes in the same fashion. After washing with toluene and methylene chloride and then drying in vacuo the resin product was examined by FT-IR in the usual manner. The spectrum thus obtained revealed the characteristic acid chloride carbonyl band in the expected position (1735.8, 1740.9, 1756.3 cm$^{-1}$) albeit in this case distinguished by a significantly greater intensity than encountered in previous crops of 4 prepared via SOCl$_2$.

Additional evidence in support of this conclusion was obtained from a subsequent experiment in which a variation of the (COCl)$_2$ method just described was carried out. In this modified version the use of (COCl)$_2$ was augmented by the addition of a small amount of pyridine, which serves in the capacity of a catalyst by removing HCl from the reaction medium thereby shifting the equilibrium toward the product acid chloride. Since pyridine hydrochloride is insoluble in neat toluene, which is the liquid phase employed previously, it was in the course of the procedure found necessary to adjust for this by carrying out the (COCl)$_2$-pyridine treatment in a mixture of toluene and chloroform, the latter a solvent in which pyridine hydrochloride is freely soluble. Accordingly, while swollen in toluene the polymeric cinnamic acid 3 was treated first with a catalytic amount of pyridine (2 drops) followed by a large excess of (COCl)$_2$ (140 eq) and the resultant mixture agitated at room temperature for 60 minutes, during which time mixing became progressively more difficult due to the accumulation of insoluble pyridinium chloride. The liquid phase was then removed and the resin treated a second time for 60 minutes with fresh pyridine-(COCl)$_2$ in the same amounts using a modified solvent combination of 2:1 (v/v) CHCl$_3$-toluene which was adequate to solubilize the pyridinium salt by-product. The resin product was subsequently washed thoroughly with chloroform, toluene, and methylene chloride, then dried in vacuo prior to analysis by FT-IR. The spectrum obtained in this case displayed a very strong acid chloride band at 1747.9 cm$^{-1}$ of even greater intensity than the earlier (COCl)$_2$-derived product discussed above. Based on this evidence the use of SOCl$_2$ was discontinued in favor of (COCl)$_2$ in all subsequent preparations of polymer-bound acid chlorides.

The Polymer-Bound Benzoic Acid System

The preceding described the preparation of polymeric-mixed anhydrides such as 5b and 5c for the purpose of establishing the practicality of this class of reagents in terms of peptide synthesis. However, the key synthetic step involving conversion of the polymer-bound cinnamoyl chloride 4 to the corresponding mixed anhydride product was found to suffer from disappointingly low yields. The acylating potential of 4 was not commensurate with expectations. It was decided to seek improved results by employing a different polymeric acid chloride in place of 4. The use of a benzoic acid moiety instead of cinnamic acid as the link to the polymeric support presented itself as a reasonable alternative in view of findings that indicated that monomeric mixed anhydrides of N-blocked amino acids derived from toluoyl chloride gave results quite comparable to those obtained from cinnamoyl chloride.

Figure 5:
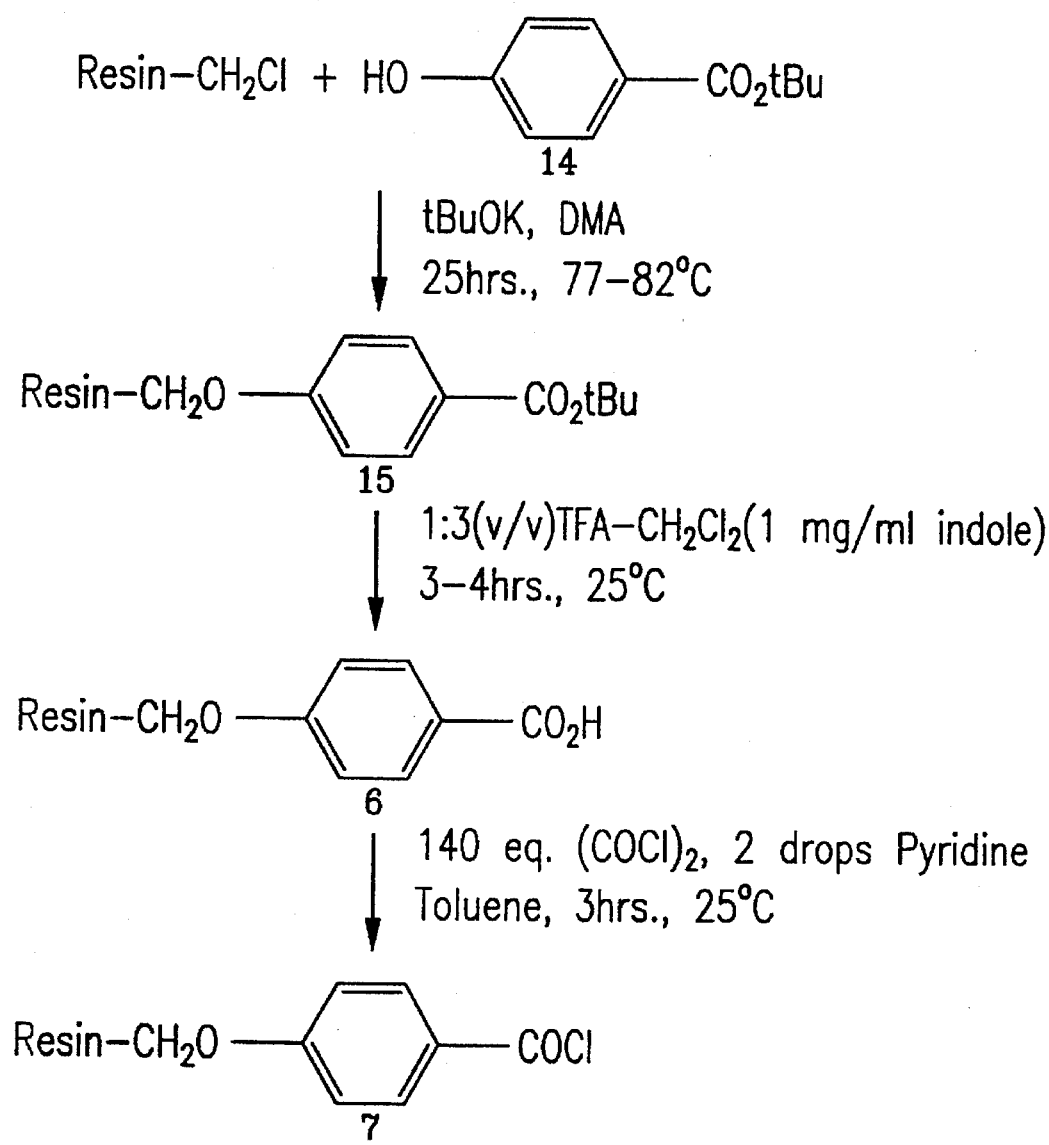
FIG. 5 is an illustration of the synthesis of the polymer-bound benzoyl chloride 7.

Accordingly, as illustrated in FIG. 5, preparation of the polymeric benzoyl chloride 7 was undertaken in a manner quite analogous to that employed previously for the synthesis of 4. Also as before, the resin was characterized at each stage of the process by FT-IR spectroscopy. Covalent attachment of the benzoic acid nucleus to the polymeric support was achieved by employing the same adaptation of the Wang O-alkylation method as used in preparation of the tert-butyl p-alkoxycinnamate resin 10. In this case, tert-butyl p-hydroxybenzoate 14 was treated with tBuOK in DMA to form the corresponding potassium phenolate salt, which was immediately reacted in a molar ratio of 2.5:1.0 with chloromethylated Merrifield resin (3.30% Cl; equivalent to 0.93 meq Cl/g resin) at 77°–82° C. for 25 hours. The product resin was washed and dried in the usual manner, then analyzed by FT-IR. As expected, the resultant spectrum displayed a strong carbonyl band at 1709.5 cm$^{-1}$, clearly representing a polymer-bound carboxylic ester functionality, thus confirming the formation of the desired tert-butyl p-alkoxybenzoate resin 15.

The tert-butyl ester protecting group was removed to yield the free carboxyl by exposure of 15 to 1:3 TFA-CH$_2$Cl$_2$ (v/v; 1 mg indole/ml) as follows. The resin was agitated with the TFA solution for 70 minutes at room temperature, after which the liquid phase was filtered off and the resin treated with fresh TFA-CH$_2$Cl$_2$ in the same fashion an additional two times. Upon analysis by FT-IR, the resin product displayed a carbonyl absorption pattern entirely consistent with previous data for polymer-bound carboxyl groups, thereby substantiating the posited conversion of 15 to the corresponding benzoic acid 6. Two closely associated bands were evident in the FT-IR spectrum, one of considerable strength at 1686.6 cm$^{-1}$ and another of slightly less intensity appearing at 1725.2 cm$^{-1}$. By analogy with the spectral data described previously for the p-alkoxycinnamic acid resin 3 it seemed clear that the larger band at 1686.6 cm$^{-1}$ was representative of the pendant carboxyl groups in a hydrogen-bonded state while the other band at 1725.2 cm$^{-1}$ was correlated with the monomeric form of the exposed carboxyls.

On the basis of the results described in the preceding subsection an excess of oxalyl chloride in concert with a catalytic quantity of pyridine was employed for conversion of 6 to the corresponding polymer-bound benzoyl chloride. Although difficulties associated with insolubility of the by-product pyridine hydrochloride in neat toluene had been previously documented, these problems were considered manageable and hence did not immediately obviate the use of toluene as a solvent medium in efforts to prepare the polymeric acid chloride. Accordingly, the starting resin 6 was swollen in toluene and then treated with pyridine (2 drops) followed by (COCl)$_2$ (140 eq), after which the mixture was agitated at room temperature for 90 minutes with relatively minor interference from the insoluble pyridinium chloride side product. After the liquid phase was filtered off, the resin was washed with toluene several times and then treated with fresh pyridine-(COCl)$_2$ in the same fashion as before for an additional 90 minutes. Afterward, the product resin was washed several times with methylene chloride to remove any remaining pyridine salt and then dried in vacuo prior to analysis by FT-IR. The spectrum thus obtained confirmed the identity of the product as the polymeric benzoyl chloride 7 by the presence of two sharp peaks of significant intensity in the carbonyl region at 1739.6 cm$^{-1}$ and 1771.7 cm$^{-1}$, a situation virtually identical to that observed in the reference spectrum of monomeric benzoyl chloride where peaks at 1745 cm$^{-1}$ and 1790 cm$^{-1}$ represent the Fermi resonance and C=O stretch bands respectively.

Figure 6:
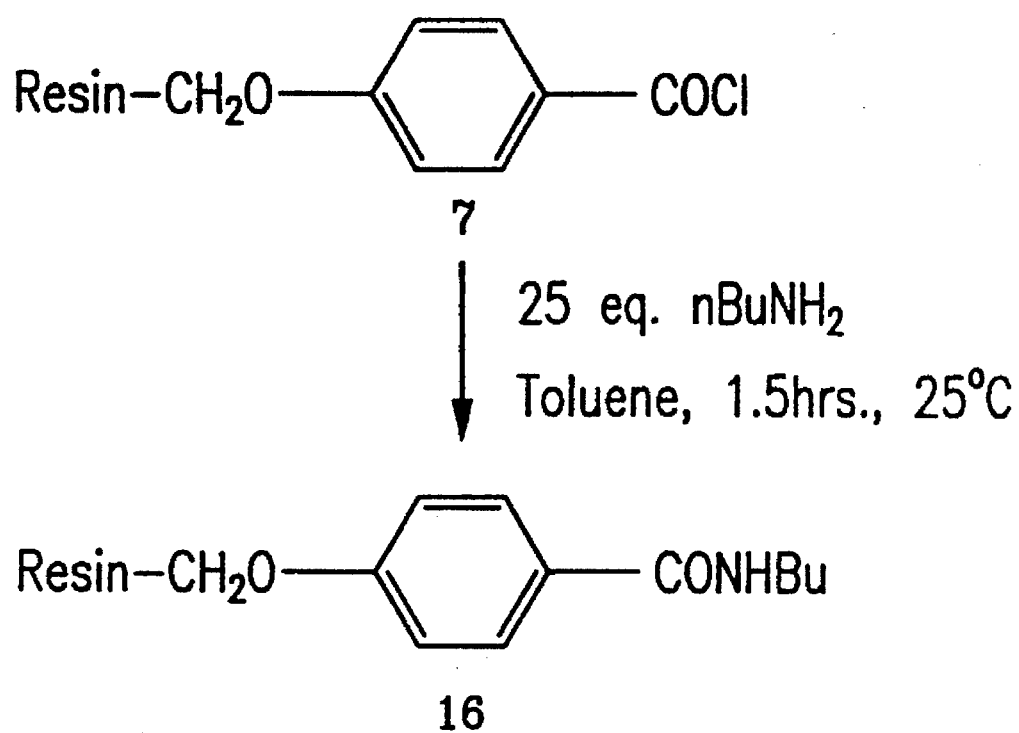
FIG. 6 is an illustration of the conversion of the polymer-bound benzoyl chloride 7 of FIG. 5 to the corresponding n-butylbenzamide.

Having prepared and characterized the polymeric benzoyl chloride 7, an assessment of its acylating potential was undertaken. Accordingly, referring now to FIG. 6, in the same manner as employed previously in the evaluation of 4, a sample of 7 was swollen in toluene, after which 25.0 eq of n-butylamine was added and the mixture agitated at room temperature for 90 minutes. The resin was washed with toluene and methylene chloride, dried in vacuo, and analyzed in the usual fashion by FT-IR. The resultant spectrum displayed a carbonyl band of moderate intensity marked by small yet distinct peaks at 1653.8 cm$^{-1}$ and 1663.0 cm$^{-1}$. This data helped establish the identity of the resin product as the polymer-bound n-butyl benzamide 16 on the basis of very similar spectral data observed for the analogous n-butyl cinnamide 17, which had been previously characterized as part of the work summarized above.

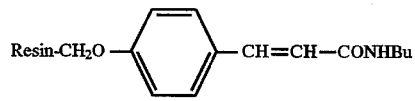

With regard to the synthesis of polymeric mixed anhydrides, a new crop of the polymeric benzoyl chloride resin 7 was prepared using a new method based on the t-butyldimethylsilyl ester procedure of Wissnet and Grudzinskas, A. Wissner, G. V. Grudzinskas, *J. Org. Chem* 43, 3972–3974 (1978). A new variation of the (COCl)$_2$ method was employed on this occasion, which utilized as an intermediate the imidazolium salt of the polymeric benzoic acid 6 and employed DMF rather than pyridine as a catalyst. The differences in this synthetic approach notwithstanding, the resin product thus obtained was confirmed as the authentic resin-bound benzoyl chloride 7 on the basis of FT-IR analysis. The authenticity of the crop of 7 prepared in this manner was confirmed by FT-IR analysis.

Figure 7:
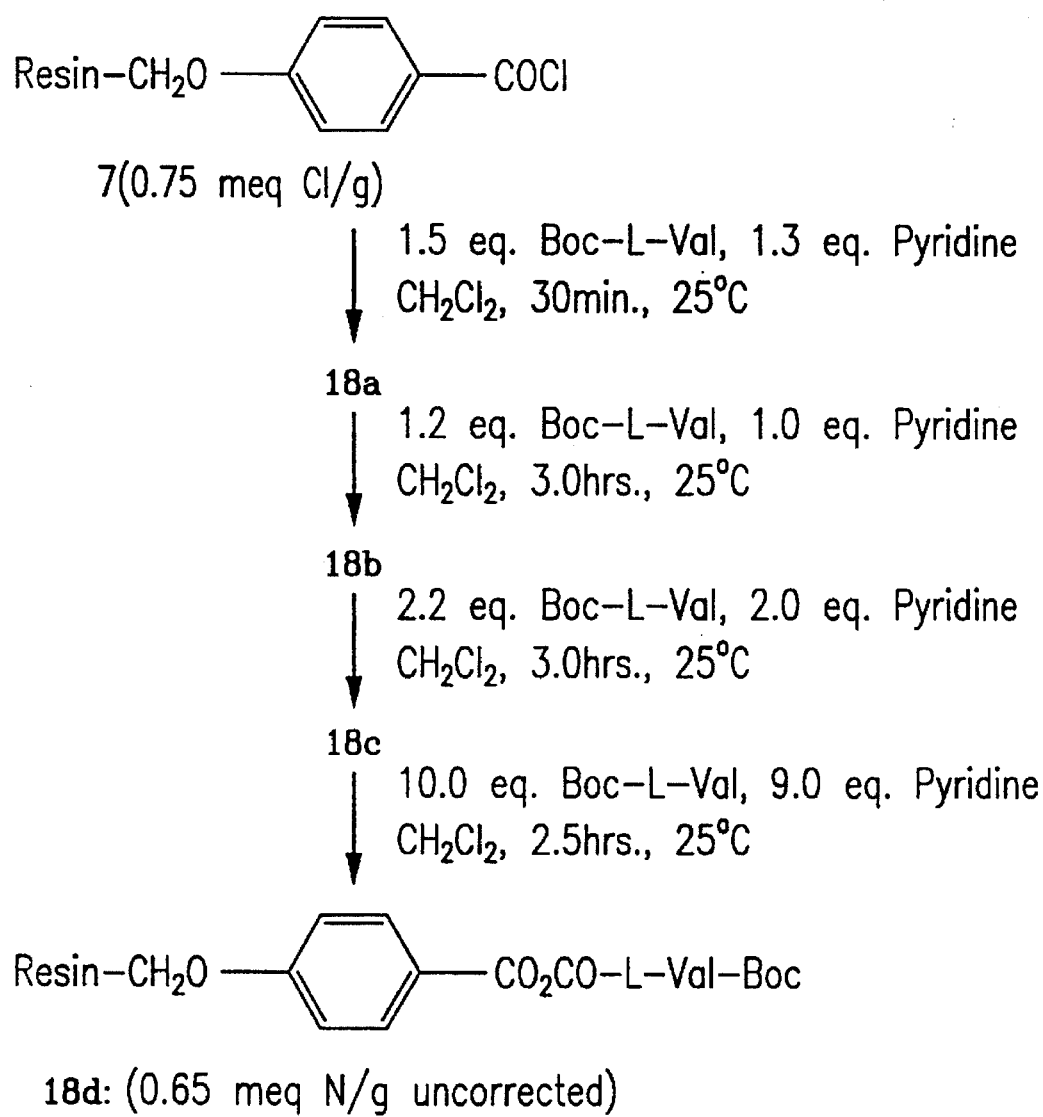
FIG. 7 is an illustration of a modified procedure for the conversion of polymer-bound benzoyl chloride 7 to the corresponding Boc-L-Val mixed anhydride.

This crop of 7 was then treated sequentially with fresh portions of pyridinium Boc-L-Val to yield a series of resin intermediates as summarized in FIG. 7. FT-IR analysis of the resin at each stage was carried out, and considerable differences were apparent upon proceeding from the spectrum of one intermediate to the next. What emerged from this data was a spectral record which vividly documented the gradual disappearance of the acid chloride bands of 7 at 1739.5 cm$^{-1}$ and 1771.5 cm$^{-1}$ in concert with the concommitant appearance of mixed anhydride bands of 18 at 1722.1 cm$^{-1}$, 1787.0 cm$^{-1}$, and 1802.5 cm$^{-1}$, culminating in a carbonyl absorption pattern marked by strong bands at 1722.4 cm$^{-1}$ and 1802.9 cm$^{-1}$ in which the previously noted band at 1787.0 cm$^{-1}$ is reduced to a shoulder on the latter.

The validity of this interpretation received additional support from the synthesis and subsequent analysis by FT-IR of the monomeric mixed anhydride 20 derived from the condensation of benzoyl chloride and the pyridine salt of Boc-L-Val.

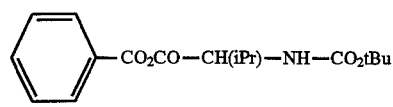

The FT-IR spectrum of 20 had a carbonyl absorption pattern marked by strong bands at 1709. cm$^{-1}$ (shoulder peak at 1733.7 cm$^{-1}$) and 1806.3 cm$^{-1}$ (shoulder peak at 1787.6 cm$^{-1}$) which is very similar to that of the intermediate 18d. This is consistent with the result observed previously for compound 11 which was at that time prepared for purposes of comparison with its polymer-bound analog 5c.

Figure 8:
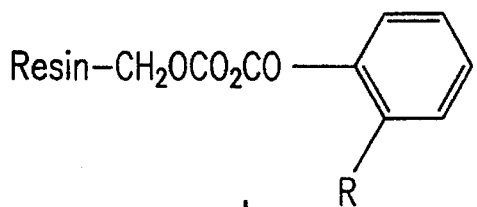
FIG. 8 is an illustration of the prior art methods of formation of symmetrical anhydrides from polymer-bound mixed anhydrides.
Figure 8:
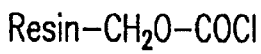
Figure 8:
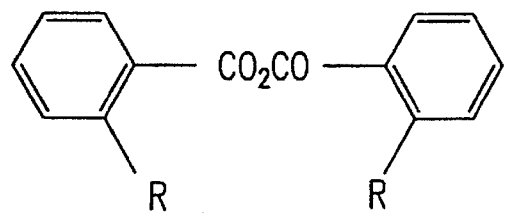

One particularly interesting aspect of the data summarized in FIG. 7 is that it runs counter to previously published findings. As illustrated in FIG. 8, on two separate occasions Digenis and co-workers had observed that polymer-bound mixed carbonic-carboxylic anhydrides were not stable under conditions of exposure to the trialkylammonium salts of the parent carboxylic acids. Under these circumstances, high yields of the corresponding symmetrical carboxylic acid anhydrides were observed. This observation does not appear to hold, however, for the Boc-L-Val polymeric mixed anhydride 18 as evidenced by the data in FIG. 7, which indicates that exposure of the intermediate 18c to 9.0 eq of pyridinium Boc-L-Val for 2.5 hours does not result in any appreciable loss of Boc-L-Val from the resin in the form of its symmetrical anhydride 21.

Boc-HN-CH(iPr)-CO$_2$CO-CH(iPr)-NH-Boc (21)

Figure 9:
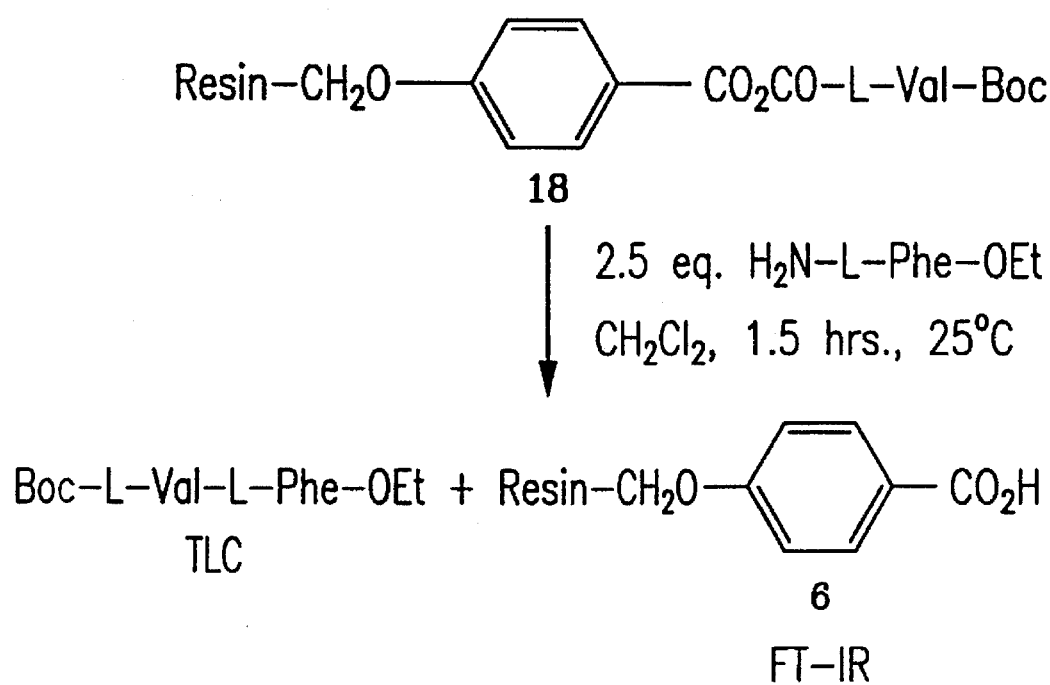
FIG. 9 is an illustration of the synthesis of the dipeptide Boc-L-Val-L-Phe-OEt from the polymeric mixed anhydride 18.

Having once established that the polymeric mixed anhydride 18 could be prepared from 7 in good yield, the focus of attention shifted to the matter of evaluating the acylating ability of 18. A preliminary assessment of this was readily achieved by treating the crop of 18 above with the amine component H$_2$N-L-Phe-OEt. The experimental details are summarized in FIG. 9 and involve the exposure of 18 to H$_2$N-L-Phe-OEt (2.5 eq) for 90 minutes at room temperature. Afterward, the liquid phase was isolated from the resin by filtration and subsequently examined by TLC for the presence of the desired product Boc-L-Val-L-Phe-OEt. As expected, the TLC data confirmed the presence of Soc-L-Val-L-Phe-OEt and in addition showed a very small amount of Boc-L-Val—presumably derived from the wrong-way opening of 18 —to be present as well. This result suggested that attack by the amine nucleophile at the amino acid carbonyl of 18 is predominant, but apparently not exclusive. Nonetheless, since the desired regioselectivity of coupling was clearly evident in this case, the presence of a small amount of Boc-L-Val was not considered a major concern in view of the fact that this by-product could be easily removed from the product Boc-L-Val-L-Phe-OEt by simple aqueous extraction. Additional data in support of the apparent regioselectivity displayed by the nucleophile H$_2$N-L-Phe-OEt was obtained by FT-IR analysis of the spent resin recovered from this experiment; after reaction the resin has reverted back to its carboxylated form in accordance with expectations and shows little evidence for the presence of the amide band that would result from significant levels of misdirected attack by the amine H$_2$N-L-Phe-OEt at the polymeric mixed anhydride.

Figure 10:
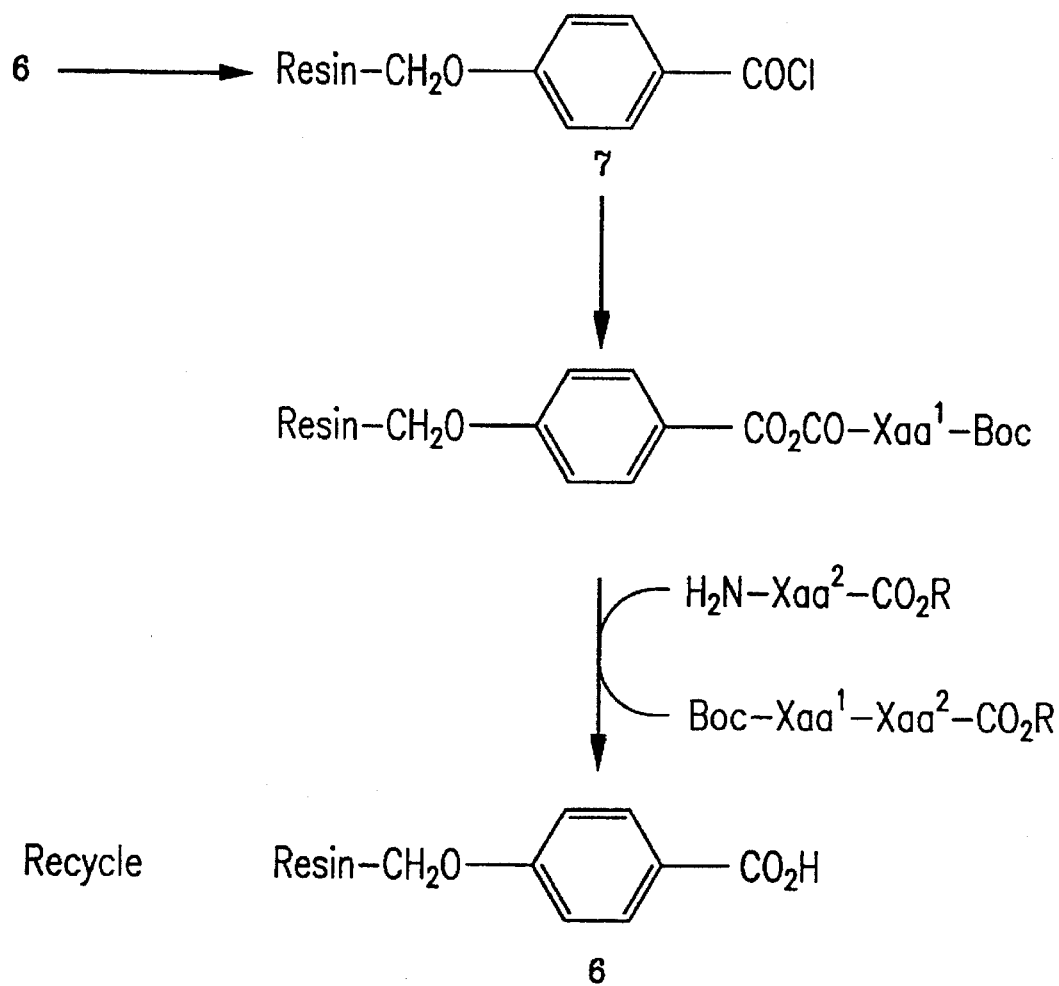
FIG. 10 is an illustration of a proposed recycling of polymeric mixed anhydrides after use.

An important consequence of this particular result is that it lends credence to recycling the resin after use, a notion which had seemed theoretically reasonable in view of the fact that, upon completion of the coupling reaction, the resin should be largely in its carboxylated form (i.e., 6) which is precursor to the polymer-bound acid chloride species 7 from which the polymeric mixed anhydride reagent is derived. This recycling scheme is depicted in FIG. 10, and as the FT-IR results suggested, the used resin recovered after its participation in a coupling reaction had sufficient pendant carboxyl groups available to permit recycling it to the benzoyl chloride form 7. It was subsequently confirmed that resin recovered under such circumstances can in fact be recycled to the polymeric benzoyl chloride 7.

Peptide Synthesis With the Polymer-Bound Benzoic Acid System

Figure 11:
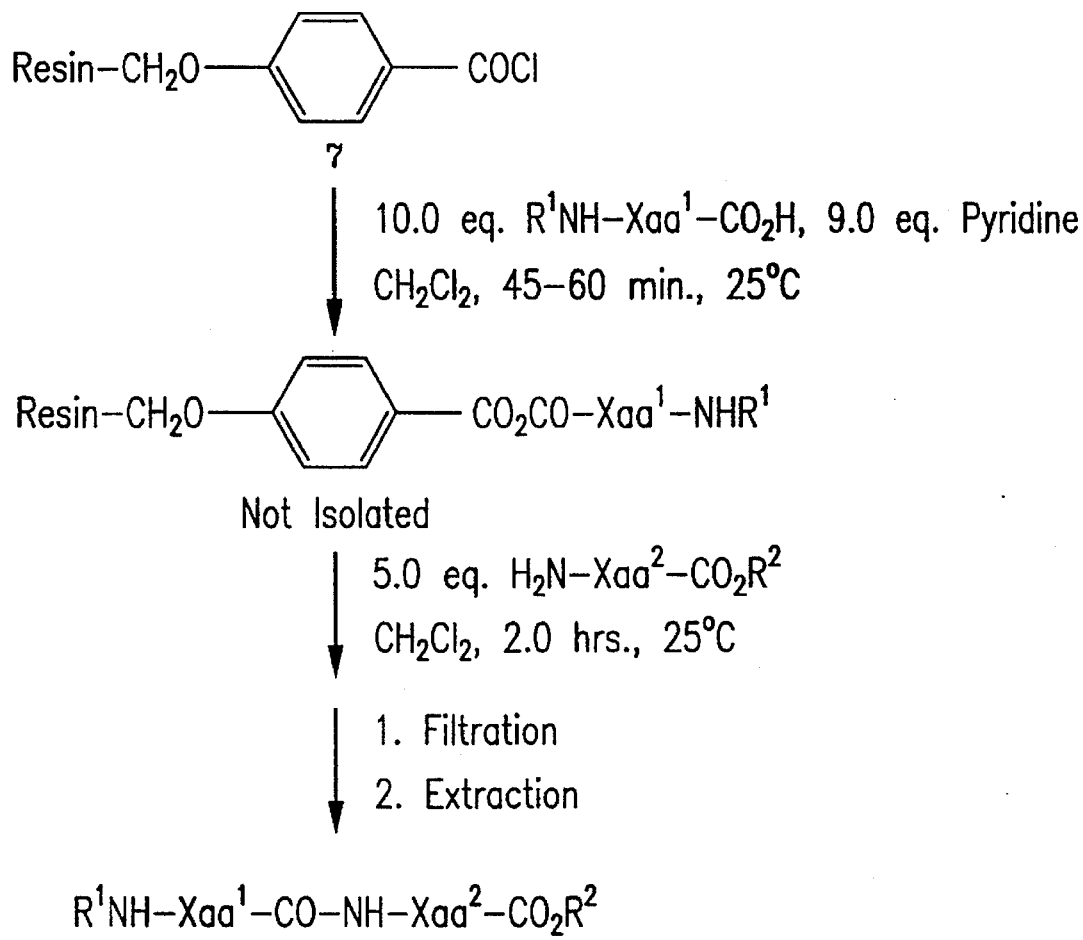
FIG. 11 is an illustration of the synthesis of protected peptides via polymeric mixed anhydrides derived from polymer-bound benzoyl chloride 7.

On the basis of the information accumulated from work completed to date, a protocol for the synthesis of protected peptides via polymeric mixed anhydrides derived from benzoyl chloride 7 has been formulated as summarized in FIG. 11. One feature of the approach as presented is that as a matter of convenience the intermediate mixed anhydride is not isolated in the strict sense but is instead washed several times in the reaction vessel and then reacted directly with the amine component. It is clear, however, from previous work with compounds 5b and 18 that such polymeric mixed anhydrides retain the ability to react with nucleophiles in the desired manner even after being isolated for characterization purposes and subsequently stored at room temperature for several days. This in turn permits flexibility with regard to the approach outlined in FIG. 11 as far as the immediate fate of the mixed anhydride is concerned by providing the option of isolating and preserving the intermediate for use at a later time. Furthermore, as will be discussed below, there is evidence to suggest that polymeric mixed anhydrides of the sort described here possess a degree of stability that will confer upon them utility as a stable form of activated carboxylic acids.

With respect to the specific scheme for peptide synthesis presented in FIG. 11, it was decided that the best means of evaluating this approach was through the preparation of several simple test peptides that could themselves be evaluated in terms of certain criteria of demonstrated importance in the field of peptide synthesis. Toward this ends a short list of target peptides was compiled as shown in Table 1 for the purpose of addressing the fundamental considerations of yield, purity, and racemization in the product, as well as the amenability of the polymeric mixed anhydride method to segment condensation. The use of the protected dipeptide Boc-L-Val-L-Phe-OEt as a tool for assessing the method in terms of product yield and purity was justified largely on the basis of convenience, given the available data on both the peptide itself and the Boc-L-Val mixed anhydride 18 from which it is derived. In similar fashion, familiarity with the Boc-L-Leu-L-Ser(OBzl)-L-Leu-D-Ala polymeric anhydride 26 made it the logical choice to participate in segment condensation studies as the carboxyl component while the commercial availability and structural simplicity of the C-protected dipeptide H₂N-Gly-Gly-OEt made it an attractive candidate for the role of amine component. As a consequence, the protected hexapeptide Boc-L-Leu-L-Ser(OBzl)-L-Leu-D-Ala-Gly-Gly-OEt emerged as a suitable target for synthesis. Lastly, the use of the deprotected dipeptide H₂N-Phe-L-Glu(OH)-OH for an examination of the extent of racemization that results from couplings effected via the polymeric mixed anhydride method was based on previous work of Steinauer et al., supra, who had developed a reversed-phase HPLC system for the separation and quantitation of a series of diastereomeric peptide pairs, including the L,L and D,L forms of H₂-N-Phe-Gly(OH)-OH.

TABLE 1

Evaluation of the Polymeric Mixed Anhydride Method Via the Synthesis of Selected Target Peptides

| Parameter to be Evaluated | Target Peptide |
|---|---|
| Yield (Dipeptide) | Boc—L—Val—L—Phe—OEt |
| Degree of Racemization | H₂N—D—Phe—L—Glu(OH)—OH |
| Segment Condensation | Boc—L—Leu—L—Ser(OBzl)—L—Leu—D—Ala—Gly—Gly—OEt |

The preparation of Boc-L-Val-L-Phe-OEt in accordance with the scheme presented in FIG. 11 was carried out in the following manner. A weighed quantity of polymeric benzoyl chloride 7 (0.57 meq Cl/g resin) was reacted with 9.0 eq of the pyridine salt of Boc-L-Val in methylene chloride for 45 minutes to generate the mixed anhydride 18, which was not isolated. After several methylene chloride washes in the reaction vessel the polymeric intermediate was treated with the amine component H₂N-L-Phe-OEt (5.0 eq) in methylene chloride for 2 hours. At the end of that time the liquid phase of the reaction mixture was separated from the resin by filtration and subsequently extracted with dilute aqueous acid and base respectively to yield a methylene chloride solution, which upon TLC analysis showed a single spot of $R_f$ 0.92. After removal of the methylene chloride and drying in vacuo, the product was isolated in the form of an oil. This material was readily confirmed as the desired Boc-L-Val-Phe-OEt on the basis of elemental analysis and FT-IR and NMR spectral data. The calculated yield of product based on benzoyl chloride 7 as limiting reagent was 68.4%, a figure quite consistent with the yields of polymeric mixed anhydrides derived from benzoyl chloride resins of moderate Cl content.

As was done previously, the spent resin from this coupling was retained and subsequently analyzed by FT-IR. The resultant spectrum indicated on the basis of moderate intensity carbonyl bands at 1686.7 cm⁻¹ and 1719.7 cm⁻¹ that the resin had largely reverted back to its carboxylated form (i.e., 6) although it may be noted that the presence of a discernable signal at 1708.5 cm⁻¹ suggested the possibility of a small percentage of ester functions on the resin as well. In order to address the issue whether or not spent polymers of this type can be recycled to the benzoyl chloride form, a portion of this resin was subjected to the (COCl)₂-pyridine treatment using methylene chloride as solvent. Upon examination by FT-IR the product gave evidence for substantial regeneration of acid chloride functionalities.

The attempted synthesis by segment condensation of the protected hexapeptide Boc-L-Leu-L-Ser(OBzl)-L-Leu-D-Ala-Gly-Gly-OEt was undertaken in a manner completely analogous to the above synthesis of Boc-L-Val-L-Phe-OEt. The polymeric mixed anhydride intermediate 26 was prepared from the benzoyl chloride 7 (0.65 meq Cl/g resin) by treatment of the latter with the pyridinium salt of 25

26

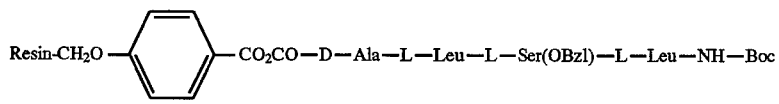

Boc-HN-L-Leu-L-Ser(OBzl)-L-Leu-D-Ala-CO₂H    (25)

(9.0 eq) in methylene for 2.0 hours, after which 26 was immediately reacted with the amine component H₂N-Gly-Gly-OEt (6.0 eq) in methylene chloride for 2.0 hours. The liquid phase was removed from the resin by filtration and extracted in the same fashion as before; subsequent examination by TLC revealed a large, clean spot corresponding to the product at R_f 0.87, contaminated only by the slightest trace of 25 (R_f 0.75). After removal of the methylene chloride and drying in vacuo, the product was isolated as a white amorphous solid. Confirmation of this material as the desired segment condensation product Boc-L-Leu-L-Ser(OBzl)-L-Leu-D-Ala-Gly-Gly-OEt was based on FT-IR and mass spectral data. Peptide sequence analysis also provided data consistent with this conclusion.

Preparation of the peptide H₂N-D-Phe-L-Glu(OH)-OH was initiated in the usual manner by treatment of the benzoyl chloride 7 (0.69 meq Cl/g resin) with the pyridine salt of Cbz-D-Phe (9.0 eq) in methylene chloride for 60 minutes to form the intermediate polymeric mixed anhydride. In accordance with the scheme in FIG. 11, the anhydride was not isolated, but was instead reacted immediately with the amine component H₂N-L-Glu(OBzl)-OBzl in methylene chloride for 2.0 hours. Subsequent work-up of the protected dipeptide Cbz-D-Phe-L-Glu(OBzl)-OBzl via filtration, extraction, and concentration in the manner previously described for the other target peptides was subject to an unexpected complication at the extraction stage when a virtually intractable emulsion formed upon washing the methylene chloride solution of crude product with dilute aqueous acid. The difficulty was traced to the use of the p-toluenesulfonic acid (pTsOH) salt of the amine component H₂N-L-Glu(OBzl)-OBzl; incomplete removal of the pTsOH prior to the addition of H₂N-L-Glu(OBzl)-OBzl to the Cbz-D-Phe polymeric mixed anhydride permitted the unwanted introduction of the sulfonic acid into the reaction mixture where it behaved as an emulsifying agent during work-up. The pTsOH was eventually removed by conversion to a water soluble salt with triethylamine (TEA) and subsequent aqueous extraction, but the difficulties created by the emulsions prior to that point almost certainly had a significant deleterious effect on the yield of the protected dipeptide product Cbz-D-Phe-L-Glu(OBzl)-OBzl, which was ultimately isolated as an opaque white oil.

It is worth noting in this context that in the above syntheses of Boc-L-Val-L-Phe-OEt and Boc-L-Leu-L-Ser(OBzl)-L-Leu-D-Ala-Gly-Gly-OEt the hydrochloride salts of the respective amine components H₂N-L-Phe-OEt and H₂N-Gly-Gly-OEt were employed with no semblance of the difficulties encountered in the Cbz-D-Phe-L-Glu(OBzl)-OBzl synthesis. This clearly indicates that were the latter synthesis to be repeated it is quite likely that improved results would be obtained by conversion of the pTsOH-H₂N-L-Glu(OBzl)-OBzl to its hydrochloride salt prior to generation of the free amine component. The procedure of Shields et al., E. Shields et al., *J. Org. Chem*, 26, 1491 (1961), should be suitable for this purpose.

In order to remove the benzyl-based protecting groups, the Cbz-D-Phe-L-Glu(OBzl)-OBzl was treated with 20:1 anhydrous HF-anisole (v/v) at 0° C. for 35 minutes. After removal of the HF-anisole the deprotected peptide was isolated via ether precipitation and subsequent lyophilization from dilute aqueous acetic acid. The product thus obtained was shown by a modified version of the HPLC system of Steinauer et al., R. Steinauer et al., *J. Chromatogr.* 325, 111–126 (1985), to be quite pure and identical to a sample of H₂N-D-Phe-L-Glu-(OH)-OH separately prepared by the SPPS method of Merrifield. Of equal importance, it is also clear that the H₂N-D-Phe-L-Gly(OH)-OH peptide prepared via the polymeric mixed anhydride method was completely free from contamination with its L,L diastereomer, thus demonstrating the complete absence of racemized Phe residues in the product. On the basis of this result, it can be concluded that the procedure for peptide synthesis presented in FIG. 11 does permit the activation and subsequent participation of N-blocked amino acids in peptide bond-forming reactions without compromising their optical purity.

The results of the peptide syntheses are collected in Table 2. It is clear from the information thus summarized that the polymeric mixed anhydride method presented in FIG. 11 does lend itself to the synthesis of peptides of excellent purity via both the coupling of amino acids and the condensation of peptide fragments. On the basis of the preliminary data summarized in Table 2, it appears that the polymeric mixed anhydride method disclosed shows promise as a means of preparing dipeptides via the coupling of suitably protected amino acids.

TABLE 2

The Synthesis of Protected Test Peptides Via the Polymeric Mixed Anhydride Method

| Carboxyl Component | Amine Component | Product | % Yield[a] |
|---|---|---|---|
| Boc—V—OH | H₂N—F—OEt | BoC—V—F—OEt[b] | 68.4 |
| Boc—L—S(OBzl)—L—dA—OH | H₂N—G—G—OEt | Boc—L—S(OBzl)—L—dA—G—G—OEt[c] | 13.8 |
| Cbz—dF—OH | H₂N—E(OBzl)—OBzl | Cbz—dF—E(OBzl)—OBzl[d] | 17.9[e] |

[a] Based on meq Cl/g starting resin
[b] Characterized by C, H, N anal., ¹H-NMR, and FT-IR
[c] Characterized by FAB-MS and FT-IR
[d] Characterized by RP-HPLC (after HF deprotection)
[e] Conditions not optimum As noted previously these reagents have been found to retain at least a portion of their acylating potential after isolation and storage for periods of up to several days' duration. In this regard preliminary information based largely on FT-IR data has been collected for the Boc-L-Ala and Boc-L-Val polymeric mixed anhydrides 27

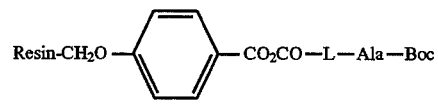

Figure 12A:
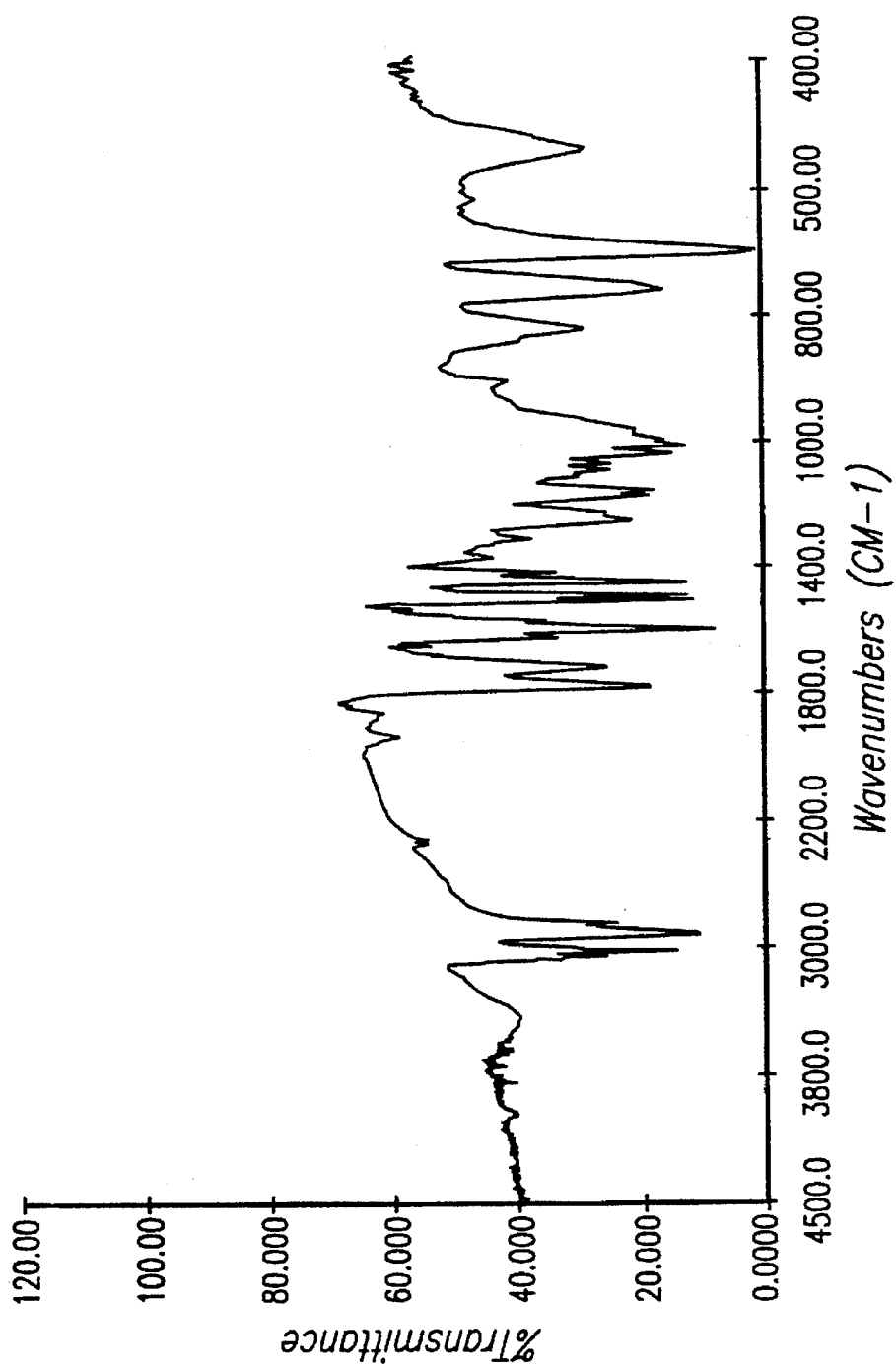
FIG. 12A is an FT-IR spectra of polymer-bound mixed anhydrides of the present invention prepared from benzoic acid and resin 3 shortly after synthesis.
Figure 12B:
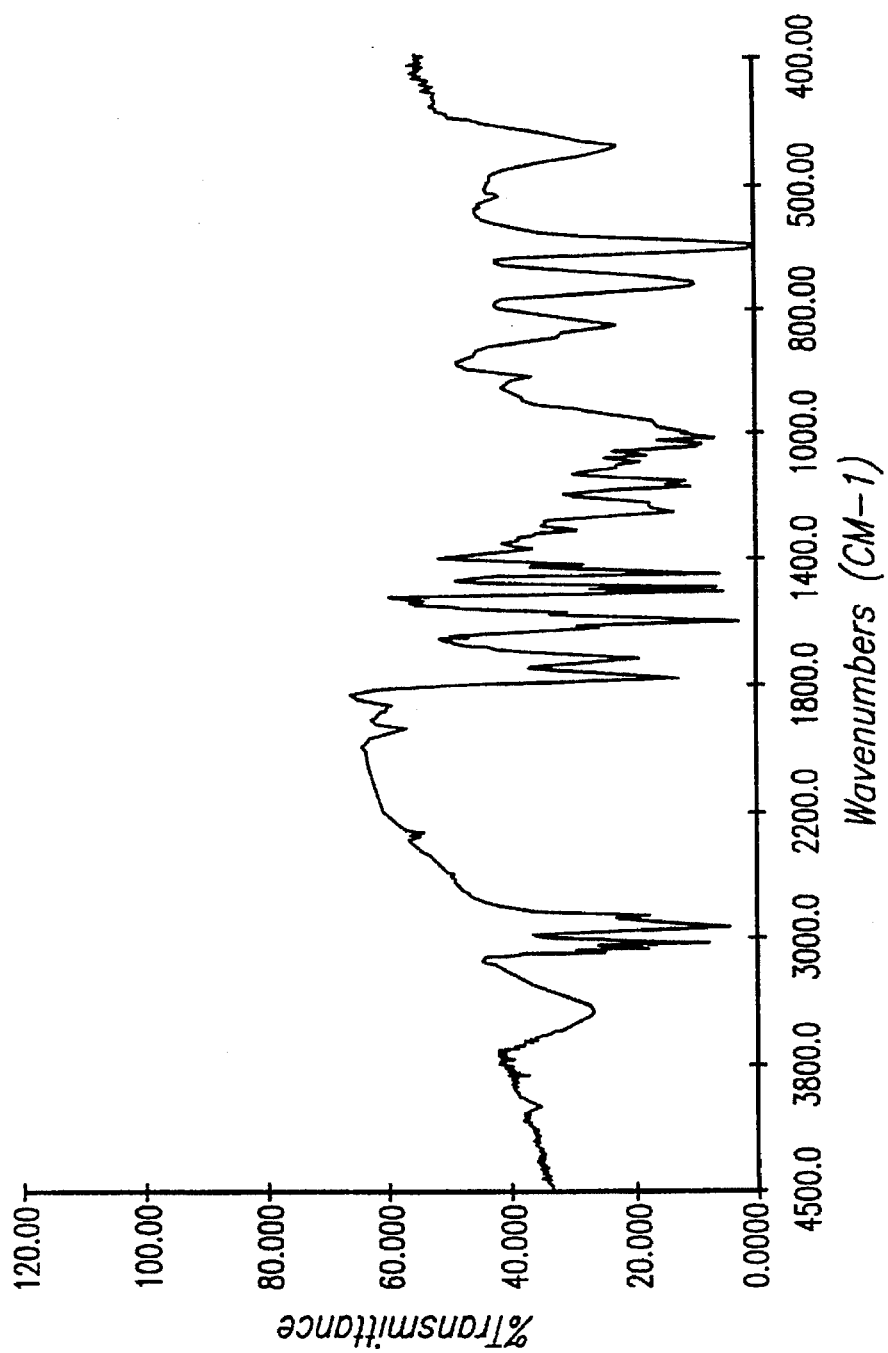
FIG. 12B is an FT-IR spectra of the polymer-bound mixed anhydride of FIG. 12A after 26 months in storage in a desiccator at room temperature.
Figure 13A:
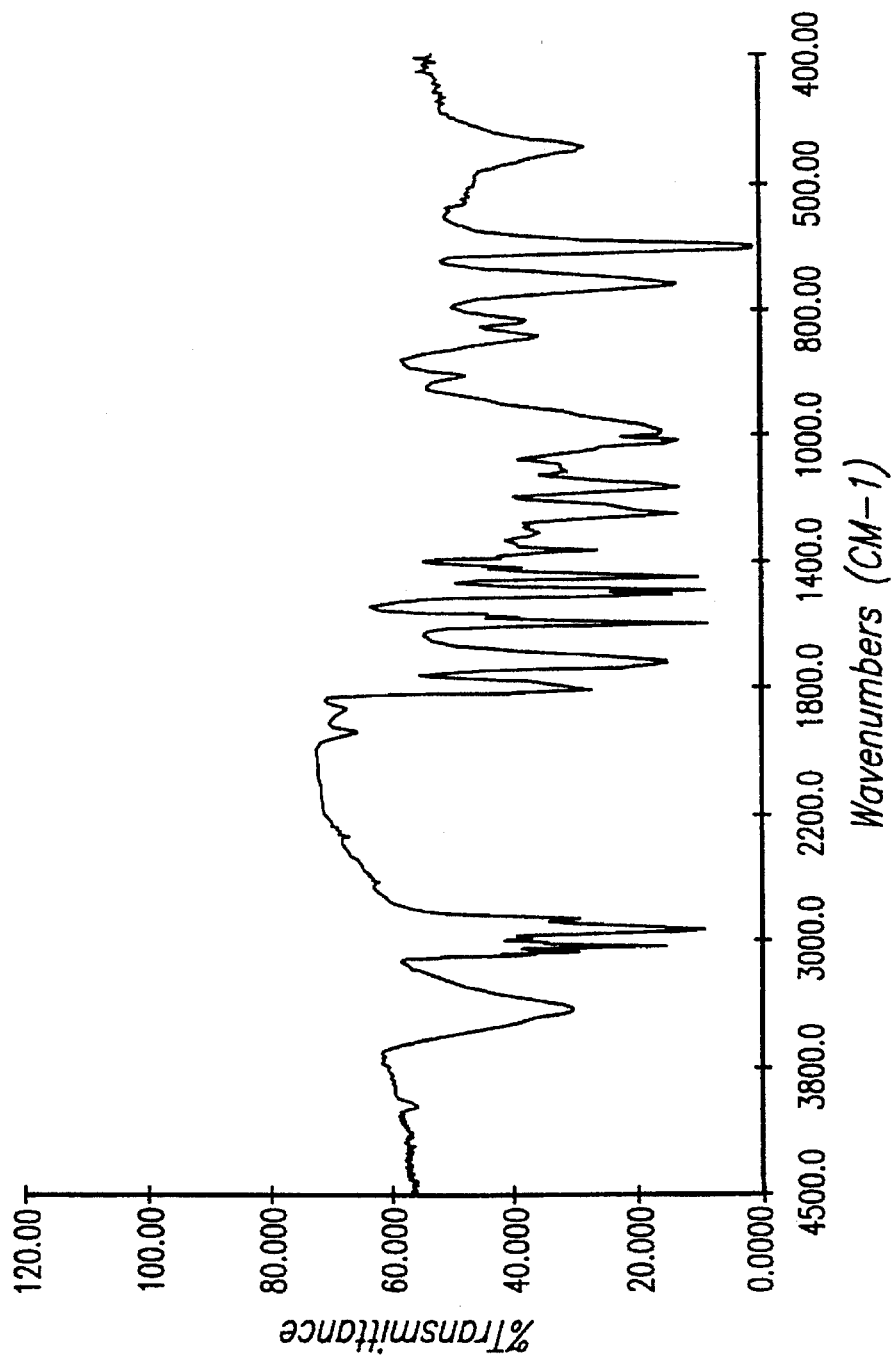
FIG. 13A is an FT-IR spectra of polymer-bound mixed anhydrides of the present invention prepared from Boc-L-Ala and resin 7 shortly after synthesis.
Figure 13B:
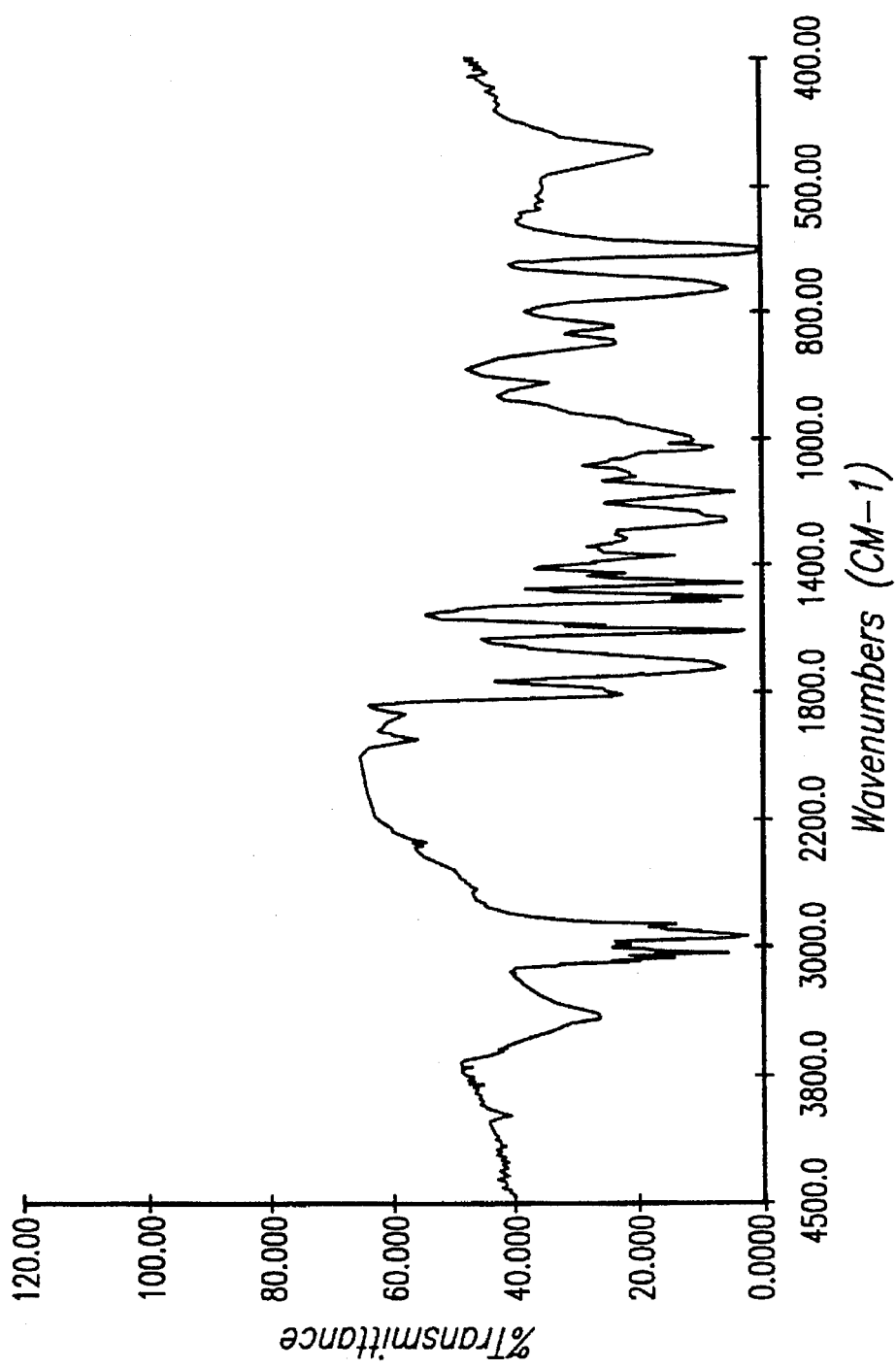
FIG. 13B is an FT-IR spectra of the polymer-bound mixed anhydride of FIG. 13A after 2 months in storage in a desiccator at room temperature.
Figure 14A:
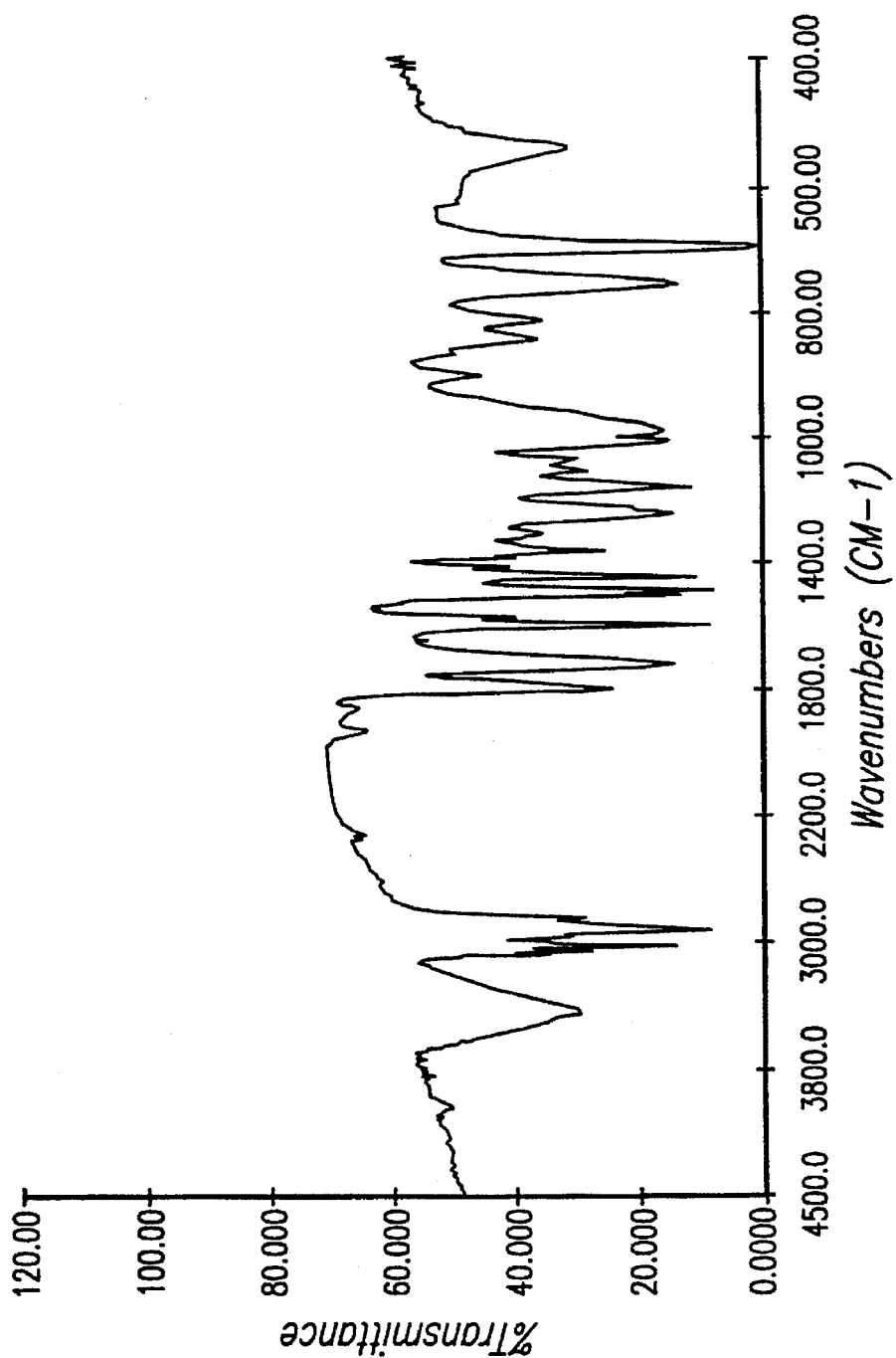
FIGS. 14A and 14B are FT-IR spectra of the polymer-bound mixed anhydride of FIG. 13A before and after 6 months in storage in a desiccator at room temperature.
Figure 14B:
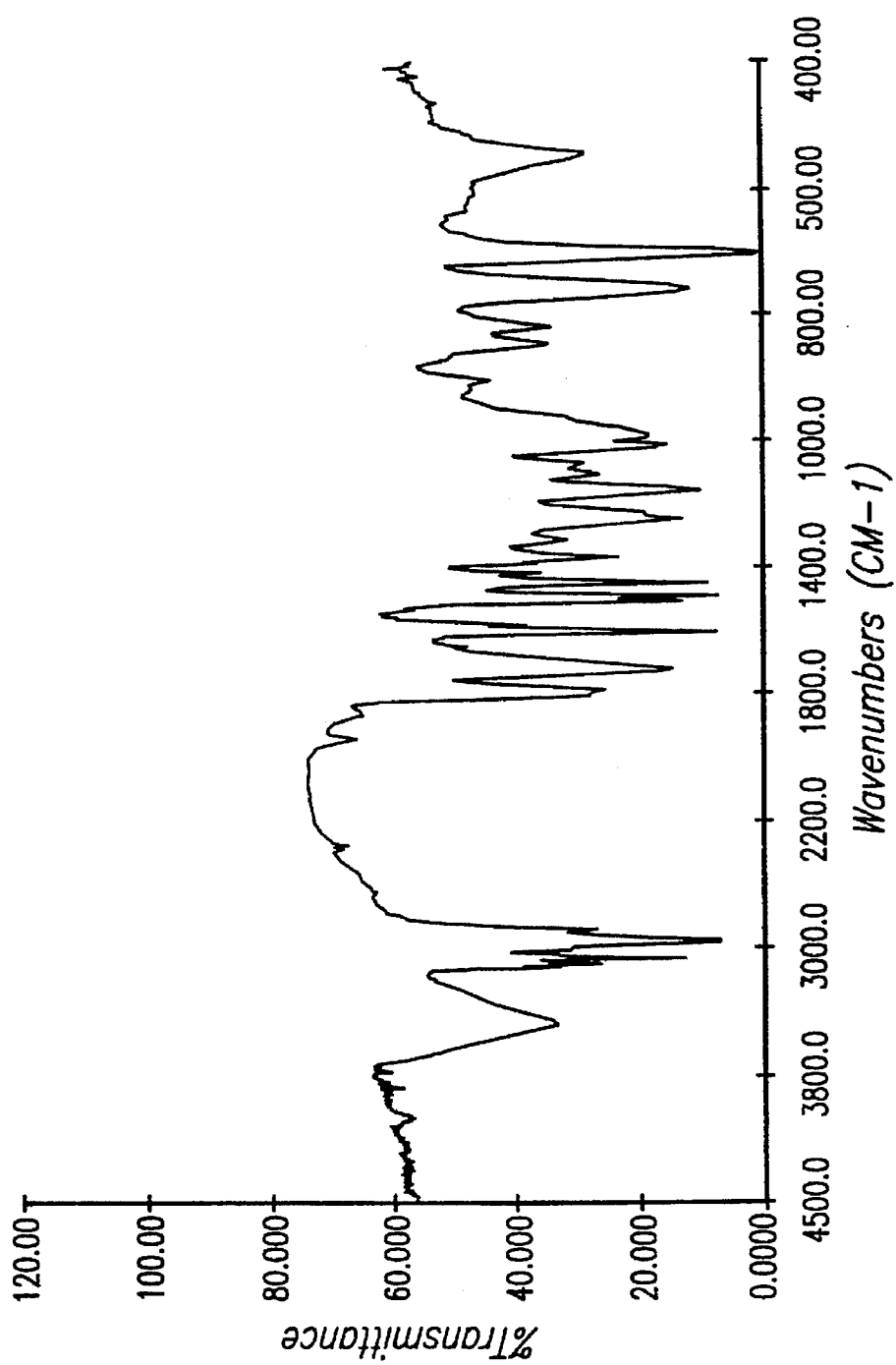

27 and 18, respectively, as well as the anhydride 5a derived from the condensation of benzoic acid and resin-bound cinnamoyl chloride 4. As illustrated in FIGS. 12–14, the spectral data indicates no discernable degradation in 5a and 27 as a consequence of desiccated storage at room temperature for periods of 26 months and two months, respectively, while only slight decomposition of 18 is suggested after storage under similar conditions for 6 months' time. Although this data is qualitative in nature and is consequently somewhat limited in the extent to which it can reflect changes in the resin, the evidence presented in FIGS. 12–14 clearly indicates the polymeric mixed anhydrides of N-blocked amino acids are largely stable for periods of greater than two months' duration while aromatic anhydrides such as 5a can be preserved virtually intact for periods on the order of several years. As described below, additional support for this conclusion was obtained by examining the reactivity of the Boc-L-Val anhydride 18 from which the data in FIG. 14 was derived.

After six months' storage at room temperature a sample of 18 was swollen in methylene chloride and subsequently treated with 3.0 eq H$_2$N-L-Phe-OEt for 2.0 hours; at the end of that time the liquid phase was removed from the resin by filtration and analyzed by TLC. The resultant chromatogram displayed a spot at R$_f$ 0.88 which was identical to that obtained for a control sample of authentic Boc-L-Val-Phe-OEt. Although it was not possible to accurately determine the yield of Boc-L-Val-L-Phe-OEt in this case since the coupling reaction was carried out on a very small scale (<0.01 mmol), the experiment conclusively demonstrated that the polymeric mixed anhydride 18 retained at least a portion of its ability to react in the desired manner after a prolonged storage period during which no special efforts were made to protect the reagent from degradation. On the basis of this result as well as the data summarized in FIGS. 12–14, the stability exhibited by polymeric mixed anhydrides such as 18 suggests that this class of reagents may be of interest not only in the obvious sense as a means of preserving N-blocked amino acids in a highly activated state but also may offer a means of gaining insight into the properties of N-blocked amino acid mixed anhydrides in general, whether they be polymeric or monomeric in nature.

The present invention represents a new method for peptide synthesis based on the use of polymeric mixed anhydrides of N-blocked amino acids. The results thus obtained have clearly demonstrated that it is indeed possible to prepare polymeric reagents of this type and to utilize them successfully in the formation of peptide bonds. Polymeric mixed anhydrides have been successfully employed in the coupling of protected amino acids as well as the condensation of peptide segments to yield easily purified products without evidence of racemization. An additional feature of this approach which has not been explicitly noted heretofore but is a useful attribute nonetheless derives from the fact that both the activation and coupling steps as depicted in FIG. 11 can be carried out under mild conditions at room temperature, a circumstance of considerable practical importance. Given the convenience of the technique with regard to reaction set-up and product purification, it is possible to envision the principle of resin-bound mixed anhydride chemistry being successfully utilized in the preparation of protected dipeptides—and possibly other small peptides—not only on a bench scale but at the level of industrial quantities as well.

The method of the present invention is a novel approach to peptide synthesis with potential applications that are complementary to those of existing methods of SPPS. In particular, the preparation of the peptides described herein represents the first instance in which polymer-bound mixed carboxylic-carboxylic anhydrides have been used to effect peptide bond formation.

While the invention has been illustrated and described in detail in the drawings and foregoing description, the same is to be considered as illustrative and not restrictive in character, it being understood that only the preferred embodiments have been described and that all changes and modifications that come within the spirit of the invention are desired to be protected. For example, early experiments in our laboratory with monomeric acid chlorides and caroxylate salts of wide variety (W. K. Fife, Z.-d. Zhang, *J. Org. Chem.* 1986, 51, 3744. W. K. Fife, Z.-d. Zhang, *Tetrahedron Lett*, 1986, 27, 4933. W. K. Fife, Y. Xin, *J. Am. Chem. Soc.* 1987, 109, 1278) have confirmed the merit of activating carboxylic acids via mixed anhydrides. Thus, the method of this invention can be utilized to activate, for subsequent derivatization, salts of a wide variety of carboxylic acids that contain no nucleophilic groups (e.g., free amino, hydroxyl) in addition to the carboxylate group.

What is claimed is:

1. A stable reagent for peptide synthesis, comprising a polymer-bound mixed carboxylic-carboxylic anhydride of N-blocked amino acids derived from a recyclable polymer-bound carboxylic acid and produced by (a) converting a polymer-bound recyclable carboxylic acid to the corresponding acid halide, and (b) reacting the acid halide of step (a) with an N-blocked amino acid salt generated in situ with a weak, non-acylatable base, thereby activating the N-blocked amino acid through conversion to a polymer-bound mixed carboxylic-carboxylic acid anhydride of the N-blocked amino acid.

2. The reagent of claim 1 wherein the recyclable, polymer-bound carboxylic acid from which said polymer-bound acid halide is derived is selected from the group consisting of polymer-bound o-, m-, and p-alkoxycinnamic acids and polymer-bound o-, m-, and p-alkoxybenzoic acids, whereby when said polymer-bound acid halide is reacted with said N-blocked amino acid salt a spacer arm linkage is provided that separates the reactive acid halide and subsequent mixed carboxylic-carboxylic anhydride groups from the polymer to permit selective, rapid and efficient access of solution reagents to them.

3. The reagent of claim 1 which is obtained by converting a polymer-bound cinnamic acid to the corresponding cinnamoyl chloride, and wherein a spacer arm is provided that separates the reactive cinnamoyl chloride and subsequent mixed carboxylic-carboxylic anhydride groups from the polymer to permit selective, rapid and efficient access of solution reagents to them.

4. The reagent of claim 1 which is obtained by converting a polymer-bound benzoic acid to the corresponding benzoyl chloride, and wherein a spacer arm is provided that separates the reactive benzoyl chloride and subsequent mixed carboxylic-carboxylic anhydride groups from the polymer to permit selective, rapid and efficient access of solution reagents to them.

5. The reagent of claim 3 wherein the polymer from which the polymer-bound cinnamoyl chloride is derived is a Merrifield chloromethylated polystyrene resin.

6. The reagent of claim 3 wherein the polymer from which the polymer-bound benzoyl chloride is derived is a Merrifield chloromethylated polystyrene resin.

7. A method for the synthesis of protected peptide derivatives of N-blocked amino acids comprising the steps of:

(a) reacting a polymer-bound acid halide of formula I

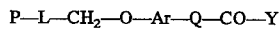
   P—L—CH$_2$—O—Ar—Q—CO—Y    I with an amino acid salt of formula II

   R$^1$NH-Xaa$^1$-CO$_2$M    II to generate a polymer-bound mixed carboxylic-carboxylic anhydride of formula III

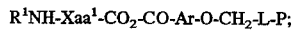
   R$^1$NH-Xaa$^1$-CO$_2$-CO-Ar-O-CH$_2$-L-P;    III (b) reacting said polymer-bound mixed carboxylic-carboxylic anhydride with an amino acid ester of formula IV

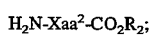
   H$_2$N-Xaa$^2$-CO$_2$R$_2$;    IV to generate a peptide derivative of formula V $R^1NH\text{-}Xaa^1\text{-}CO\text{-}NH\text{-}Xaa^2\text{-}CO_2R^2;$  V and a spent polymer of formula VI $P\text{—}L\text{—}CH_2\text{—}O\text{—}Ar\text{—}Q\text{—}COOH;$  VI (c) separating the liquid phase of the reaction mixture from the spent polymer by filtration; and (d) extracting from said liquid phase a peptide derivative of formula V;

wherein in said method the substituent variables correspond as follows:

P is a polymeric solid support;

L is a covalent bond or a linker moiety;

Ar is a phenylene moiety, optionally substituted with an alkoxy group;

Q is a covalent bond or —CH=CH—;

$R^1$ is an amino blocking or protecting group;

$R^2$ is a carboxyl blocking or protecting group;

Y is a halogen;

-NH-$Xaa^1$-CO- is an amino acid residue;

-NH-$Xaa^2$-CO- is an amino acid residue; and $R^1$-NH-$Xaa^1$-$CO_2M$ is a salt of an N-blocked or N-protected amino acid.

8. The method of claim 7, further comprising regenerating the polymer-bound acid halide of formula I from the spent polymer of formula VI.

9. The method of claim 7, wherein said polymer-bound acid halide is a polymer-bound cinnamoyl chloride.

10. The method of claim 7, wherein the polymer-bound acid halide is a polymer-bound benzoyl chloride.

11. The method of claim 9, wherein the polymeric solid support is a Merrifield chloromethylated polystyrene resin.

12. The method of claim 10, wherein said polymeric solid support is a Merrifield chloromethylated polystyrene resin.

13. A method for the synthesis of protected peptide derivatives of N-blocked amino acids comprising the steps of:

(a) converting a polymer-bound recyclable carboxylic acid to the corresponding acid halide;

(b) reacting the acid halide of step (a) with an N-blocked amino acid salt generated in situ with a weak non-acylatable base, thereby activating the N-blocked amino acid through conversion to a polymer-bound mixed carboxylic-carboxylic acid anhydride of the N-blocked amino acid;

(c) reacting the polymer-bound mixed carboxylic-carboxylic acid anhydride of step (b) with an amino acid ester of the formula $H_2N\text{-}Xaa^2\text{-}CO_2R^2;$ to generate a peptide derivative of the formula $R^1NH\text{-}Xaa^1\text{-}CO\text{-}NH\text{-}Xaa^2\text{-}CO_2R^2$ and the starting polymer-bound recyclable carboxylic acid of step (a);

(d) separating the liquid phase of the reaction mixture from said polymer-bound recyclable carboxylic acid by filtration; and (e) extracting from said liquid phase the peptide derivative of step (c);

wherein in said method the substituent variables correspond as follows:

-NH-$Xaa^1$-CO- is an amino acid residue;

-NH-$Xaa^2$-CO- is an amino acid residue;

$R^1$ is an amino blocking or protecting group;

$R^2$ is a carboxyl blocking or protecting group.

14. The method of claim 13, further comprising isolating the polymer-bound recyclable carboxylic acid produced in step (c) and converting it to the corresponding polymer-bound acid halide.

15. The method of claim 13, wherein the polymer from which the polymer-bound recyclable carboxylic acid is derived is a Merrifield chloromethylated polystyrene resin.

* * * * *